US011407728B2

(12) United States Patent
Das et al.

(10) Patent No.: US 11,407,728 B2
(45) Date of Patent: Aug. 9, 2022

(54) DERIVATIVES OF EPA ENDOCANNABINOID EPOXIDES AS ANTI-INFLAMMATORY, ANTI-CANCEROUS, ANTI-ANGIOGENC AND ANTIPLATELET AGGREGATION COMPOUNDS

(71) Applicant: The Board of Trustees of the University of Illinois, Urbana, IL (US)

(72) Inventors: Aditi Das, Champaign, IL (US); Josephine E. Watson, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/648,953

(22) PCT Filed: Sep. 20, 2018

(86) PCT No.: PCT/US2018/051888
§ 371 (c)(1),
(2) Date: Mar. 19, 2020

(87) PCT Pub. No.: WO2019/060508
PCT Pub. Date: Mar. 28, 2019

(65) Prior Publication Data
US 2020/0247777 A1      Aug. 6, 2020

Related U.S. Application Data

(60) Provisional application No. 62/560,726, filed on Sep. 20, 2017.

(51) Int. Cl.
*C07D 331/02* (2006.01)
*C07D 303/46* (2006.01)
*C07D 203/08* (2006.01)
*A61P 29/00* (2006.01)

(52) U.S. Cl.
CPC ............ *C07D 331/02* (2013.01); *A61P 29/00* (2018.01); *C07D 203/08* (2013.01); *C07D 303/46* (2013.01)

(58) Field of Classification Search
None
See application file for complete search history.

(56) References Cited

U.S. PATENT DOCUMENTS

2013/0274327 A1   10/2013   Arita et al.

FOREIGN PATENT DOCUMENTS

WO   WO 2008/100977 A2   8/2008
WO   WO 2012/167133 A2   12/2012

OTHER PUBLICATIONS

Berge et al., "Pharmaceutical Salts," J Pharmaceutical Sciences, 1977, 66(1):1-19.
Bifulco et al., "Endocannabinoids as emerging suppressors of angiogenesis and tumor invasion (Review)," Oncol Rep, 2007, 17:813-816.
Boyd et al., "Rimonabant—a selective CB1 antagonist," Ann Pharmacother, 2005, 39(4):684-90.
Brown et al., "Cannabinoid receptor-dependent and -independent anti-proliferative effects of omega-3 ethanolamides in androgen receptor-positive and -negative prostate cancer cell lines," Carcinogenesis, 2010, 31(9):1584-1591.
Brown et al., "Cannabinoids and omega-3/6 endocannabinoids as cell death and anticancer modulators," Prog Lipid Res, 2013, 52(1):80-109.
Chakravarti et al., "Cannabinoids as therapeutic agents in cancer: current status and future implications," Oncotarget, 2014, 5(15):5852-5872.
Cianchi et al., "Cannabinoid Receptor Activation Induces Apoptosis through Tumor Necrosis Factor alpha—Mediated Ceramide De novo Synthesis in Colon Cancer Cells," Clinical Cancer Research, 2008, 14(23):7691-7700.
Cui et al., "The ω-3 epoxide of eicosapentaenoic acid inhibits endothelial cell proliferation by p38 MAP kinase activation and cyclin D1/CDK4 down-regulation," Br J Pharmacol, 2011, 162(5):1143-55.
D'Eliseo et al., "Omega-3 Fatty Acids and Cancer Cell Cytotoxicity: Implications for Multi-Targeted Cancer Therapy," J Clin Med, 2016, 5(2):15, 29 pages.
Di Marzo et al., "Why do cannabinoid receptors have more than one endogenous ligand?," Philosophical Transactions of the Royal Society B-Biological Sciences, 2012, 367(1607):3216-3228.
Di Marzo, "Endocannabinoids: synthesis and degradation," Rev Physiol Biochem Pharmacol, 2008, 160: 1-24.
Falck et al., "Arachidonate epoxygenase: inhibitors and metabolite analogues," Tetrahedron Letters, 1985, 26(19):2287-2290.
Fonseca et al., "Endogenous cannabinoids revisited: a biochemistry perspective," Prostaglandins Other Lipid Mediat, 2013, 102-103, 13-30.
Giang et al., "Molecular characterization of human and mouse fatty acid amide hydrolases," Proc Natl Acad Sci U S A, 1997, 94(6):2238-2242.
Goparaju et al., "Anandamide amidohydrolase of porcine brain: cDNA cloning, functional expression and site-directed mutagenesis," Biochimica Et Biophysica Acta—Molecular and Cell Biology of Lipids, 1999, 1441(1):77-84.
Guindon et al., "The endocannabinoid system and cancer: therapeutic implication," Br J Pharmacol, 2011, 163(7):1447-63.
Hald et al., "Differential effects of repeated low dose treatment with the cannabinoid agonist WIN 55,212-2 in experimental models of bone cancer pain and neuropathic pain," Pharmacol Biochem Behav, 2008, 91(1):38-46.
Hillard et al., "Characterization of the kinetics and distribution of N-arachidonylethanolamine (anandamide) hydrolysis by rat brain," Biochim Biophys Acta, 1995, 1257(3):249-56.
Hsu et al., "Anandamide-induced Ca2+ elevation leading to p38 MAPK phosphorylation and subsequent cell death via apoptosis in human osteosarcoma cells," Toxicology, 2007, 231(1):21-9.

(Continued)

Primary Examiner — Po-Chih Chen
(74) Attorney, Agent, or Firm — Michael Best & Friedrich LLP

(57) ABSTRACT

The present disclosure provides chemical compound derivatives of a class of biological lipid mediators known as endocannabinoids and methods of synthesizing the compositions. These compounds are useful for treating cancer, reducing inflammation, reducing platelet aggregation, and reducing angiogenesis.

20 Claims, 10 Drawing Sheets

(56) References Cited

OTHER PUBLICATIONS

Jarrahian et al., "Structure-activity relationships among N-arachidonylethanolamine (Anandamide) head group analogues for the anandamide transporter," J Neurochem, 2000, 74(6):2597-606.

Jaudszus et al., "Evaluation of suppressive and pro-resolving effects of EPA and DHA in human primary monocytes and T-helper cells," J Lipid Res, 2013, 54(4):923-35.

Kroeze et al., "PRESTO-Tango as an open-source resource for interrogation of the druggable human GPCRome," Nat Struct Mol Biol, 2015, 22(5):362-9.

Ladin et al., "Preclinical and Clinical Assessment of Cannabinoids as Anti-Cancer Agents," Frontiers in Pharmacology, 2016, 7:361, 18 pages.

Laviano et al., "Omega-3 fatty acids in cancer," Curr Opin Clin Nutr Metab Care, 2013, 16(2):156-61.

Lozano-Ondoua et al., "A cannabinoid 2 receptor agonist attenuates bone cancer-induced pain and bone loss," Life Sci, 2010, 86(17-18)646-53.

McDougle et al., "Anti-inflammatory ω-3 endocannabinoid epoxides," Proc Natl Acad Sci USA, 2017, 114(30):E6034-E6043.

Morisseau et al., "Naturally occurring mono epoxides of EPA and DHA are bioactive antihyperalgesic lipids," Journal of Lipid Research, 2010, vol. 7, Issue 27, 35 pages.

Nishida et al., "Angiogenesis in cancer," Vasc Health Risk Manag, 2006, 2(3):213-9.

Nithipatikom et al., "2-arachidonoylglycerol: a novel inhibitor of androgen-independent prostate cancer cell invasion," Cancer Res, 2004, 64(24):8826-30.

Roy, "Omics Approach Towards Understanding the Function of Bioactive Lipids in Osteosarcoma," Dissertation, 2017, 414 pages.

Sica et al., "Cancer related inflammation: the macrophage connection," Cancer Lett, 2008, 267(2):204-15.

Skaper et al., "Endocannabinoids in nervous system health and disease: the big picture in a nutshell," Philos Trans R Soc Lond B Biol Sci, 2012, 367(1607):3193-200.

Song et al., "CB1 cannabinoid receptor-mediated cell migration," Journal of Pharmacology and Experimental Therapeutics, 2000, 294(1):204-209.

Winkler et al., "Fatty acid amide hydrolase inhibitors confer anti-invasive and antimetastatic effects on lung cancer cells," Oncotarget, 2016, 7(12):15047-64.

Yin et al., "Lipid G protein-coupled receptor ligand identification using beta-arrestin PathHunter assay," J Biol Chem, 2009, 284(18):12328-38.

International Search Report and Written Opinion for Application No. PCT/US2018/051887 dated Jan. 22, 2019 (15 pages).

International Search Report and Written Opinion for Application No. PCT/US2018/051888 dated Jan. 24, 2019 (16 pages).

Watson et al., "Emerging Class of Omega-3 Fatty Acid Endocannabinoids & Their Derivatives", Prostaglandins Other Lipid Madiat., Aug. 2019, vol. 143, pp. 1-29.

McDougle, "Cytochrome P450 2J2 Mediated Metabolism of Omega-6 and Omega-3 Endocannabinoids", Doctoral Dissertation—Comparative Biosciences, University of Illinois at Urbana-Champaign, Nov. 2016, 213 pages.

McDougle et al., "Anti-inflammatory omega-3 Endocannabinoid Epoxides", Supporting Information Appendix for article published in Proc Natl Acad Sci USA, 2017, vol. 114, No. 30 (21 pages).

Roy et al., "Antitumorigenci Properties of Omega-3 Endocannabinoid Epoxides", Journal of Medicinal Chemistry, vol. 61, 2018, pp. 5569-5579.

DERIVATIVES OF EPA ENDOCANNABINOID EPOXIDES AS ANTI-INFLAMMATORY, ANTI-CANCEROUS, ANTI-ANGIOGENC AND ANTIPLATELET AGGREGATION COMPOUNDS

CROSS-REFERENCE TO RELATED APPLICATION

This patent application is the U.S. national stage entry, under 35 U.S.C. § 371, of International Application Number PCT/US2018/051888, filed Sep. 20, 2018, which claims the benefit of and priority to U.S. Provisional Application No. 62/560,726, filed on Sep. 20, 2017, the entire contents of each of which are hereby incorporated by reference.

BACKGROUND

Endocannabinoid epoxides (eCBs) have been found in various rat organs and have been shown to be anti-inflammatory, anti-angiogenic and to reduce platelet aggregation. However, eCBs have two hydrolysable functional groups which make them less stable in the human body. First, soluble epoxide hydrolases (sEH) hydrolyze the epoxide to inactive diol compounds and fatty acid amide hydrolase (FAAH) hydrolyzes the amide functional group to free acid, thereby reducing the molecule's biological activity. Derivatives of eCBs with improved biological stability are needed to make them better candidates for therapeutics.

SUMMARY

The present invention relates to novel endocannabinoid epoxides, their salts and pharmaceutical compositions and methods of use.

In one aspect, the invention provides a compound of formula (I), compounds or compositions of formula (I), or a pharmaceutically acceptable salt thereof,

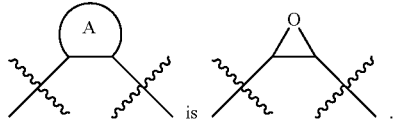

(I)

wherein,
one of $L^1$, $L^2$, $L^3$, $L^4$, and $L^5$ is

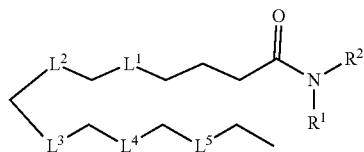

and the others of $L^1$, $L^2$, $L^3$, $L^4$, and $L^5$ are

is 3- to 6-membered ring containing at least one heteroatom selected from the group consisting of oxygen, nitrogen, and sulfur;

$R^1$ is hydrogen, $C_{1-6}$alkyl, $C_{1-6}$haloalkyl, —$C_{1-6}$alkylene-$R^{x1}$, -$G^1$, or —$C_{1-6}$alkylene-$G^1$;

$G^1$ is $C_{3-8}$cycloalkyl, $C_{3-8}$cycloalkenyl, aryl, heteroaryl, or heterocycle, wherein $G^1$ is optionally substituted with 1, 2, 3, or 4 $R^{x1}$;

$R^2$ is $C_{1-6}$alkyl, $C_{1-6}$haloalkyl, —$C_{1-6}$alkylene-$R^{x2}$, -$G^2$, or —$C_{1-6}$alkylene-$G^2$;

$G^2$ is $C_{3-8}$cycloalkyl, $C_{3-8}$cycloalkenyl, aryl, heteroaryl, or heterocycle, wherein $G^2$ is optionally substituted with 1, 2, 3, or 4 $R^{x2}$;

$R^{x1}$ and $R^{x2}$ at each occurrence are independently cyano, —OH, —$OC_{1-4}$alkyl, —$OC(O)C_{1-4}$alkyl, —$NH_2$, —$NHC_{1-4}$alkyl, —$N(C_{1-4}$alkyl$)_2$, —$NHC(O)C_{1-4}$alkyl, or —$N(C_{1-4}$alkyl$)C(O)C_{1-4}$alkyl;

provided that $R^2$ is not —$CH_2CH_2OH$ when

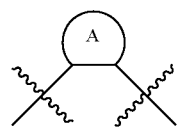

In another aspect, the invention provides a pharmaceutical composition comprising a compound of formula (I), or a pharmaceutically acceptable salt thereof, and a pharmaceutically acceptable carrier.

In another aspect, the present disclosure provides a use of a compound or composition of formula (I), or a pharmaceutically acceptable salt thereof, for treating a disease, condition, or disorder in a subject. For example, the compounds or compositions disclosed herein may be used for treating cancer, reducing inflammation, reducing platelet aggregation, reducing angiogenesis or inducing vasoconstriction or vasodilation.

In another aspect, the present disclosure provides a use of a compound or composition of formula (I), or a pharmaceutically acceptable salt thereof, for manufacturing a medicament for treating a disease, condition, or disorder in a subject. For example, the compounds or compositions disclosed herein may be used for manufacturing a medicament for treating cancer, reducing inflammation, reducing platelet aggregation, reducing angiogenesis, or inducing vasoconstriction or vasodilation.

In yet another aspect, the present disclosure provides a method of treating cancer comprising administering to a subject in need thereof a therapeutically effective amount of a compound of formula (I), or a pharmaceutically acceptable salt thereof, or a pharmaceutical composition thereof.

In yet another aspect, the present disclosure provides a method of reducing inflammation comprising administering to a subject in need thereof a therapeutically effective amount of a compound of formula (I), or a pharmaceutically acceptable salt thereof, or a pharmaceutical composition thereof.

In yet another aspect, the present disclosure provides a method of reducing platelet aggregation comprising administering to a subject in need thereof a therapeutically effective amount of a compound of formula (I), or a pharmaceutically acceptable salt thereof, or a pharmaceutical composition thereof.

In yet another aspect, the present disclosure provides a method of reducing angiogenesis comprising administering to a subject in need thereof a therapeutically effective amount of a compound of formula (I), or a pharmaceutically acceptable salt thereof, or a pharmaceutical composition thereof.

In yet another aspect, the present disclosure provides a method of inducing vasoconstriction or vasodilation comprising administering to a subject in need thereof a therapeutically effective amount of a compound of formula (I), or a pharmaceutically acceptable salt thereof, or a pharmaceutical composition thereof.

Other aspects will become apparent by consideration of the detailed description and accompanying drawings.

BRIEF DESCRIPTION OF THE DRAWINGS

The features, objects and advantages other than those set forth above will become more readily apparent when consideration is given to the detailed description below. Such detailed description makes reference to the following drawings.

Figure 1A:
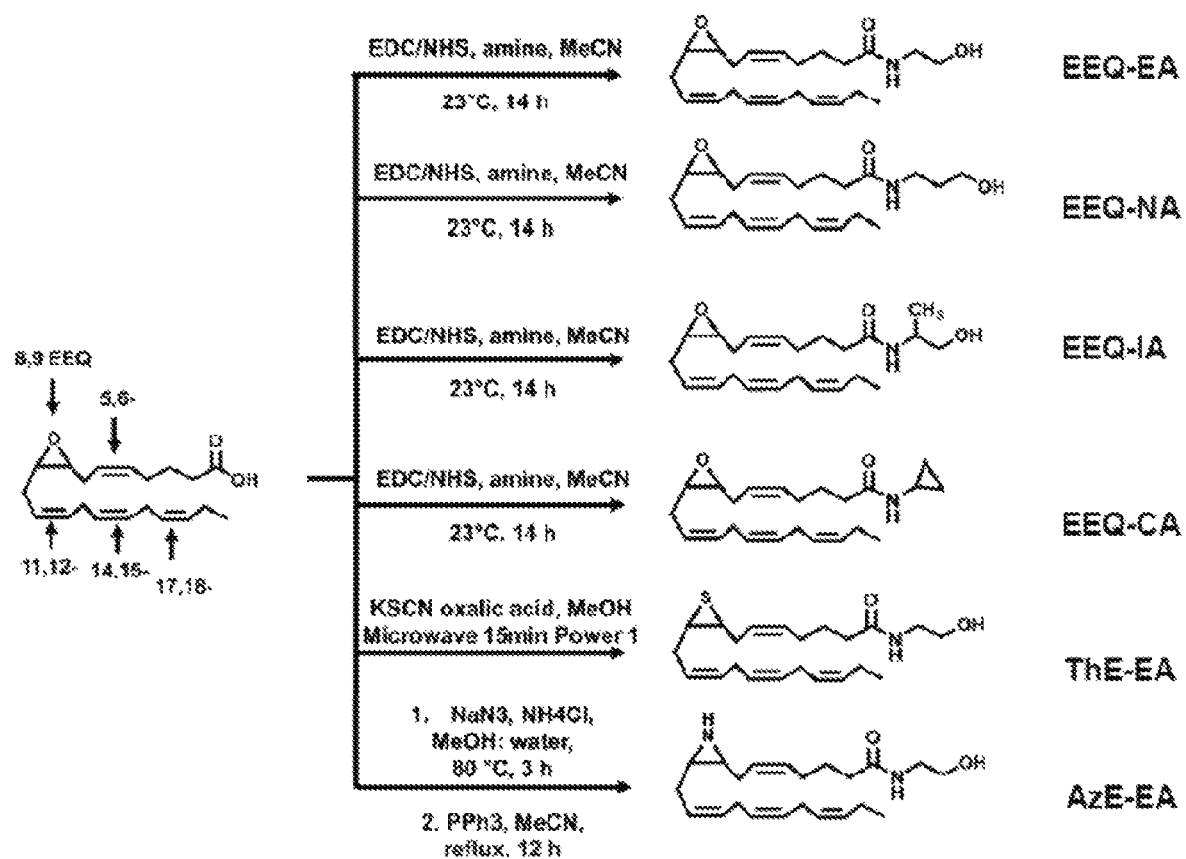
FIG. 1A shows the structures of EEQ-EA, and various epoxide, aziridine and thiirane derivatives and the corresponding syntheses from EPEA epoxide (EEQ). Epoxide derivatives, 8,9-epoxyeicosatetraenoyl-N-propylamine (EEQ-NA), 8,9-epoxyeicosatetraenoyl-isopropylamine (EEQ-IA), 8,9-epoxyeicosatetraenoyl-cyclopropylamine (EEQ-CA), were synthesized from EEQ by amine coupling with EDC/NHS in MeCN and incubated at room temperature for 14 hrs. Aziridine derivatives, i.e. 8,9-aziridine-eicosatetraenoyl-ethanolamine (AzE-EA), and thiirane derivatives, i.e. 8,9-thiirane-eicosatetraenoyl-ethanolamine (ThE-EA), are prepared as generally shown.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

By way of introduction, compounds of the invention are derivatives of a class of biological lipid mediators known as endocannabinoids. Endocannabinoid epoxides (eCBs) have been found in various rat organs and have been shown to be anti-inflammatory, anti-angiogenic and reduce platelet aggregation. However, eCBs have two functional groups that are susceptible to hydrolysis, which makes them less stable in the human body. Soluble epoxide hydrolases (sEH) convert the epoxide to inactive diol compounds and fatty acid amide hydrolase (FAAH) converts the amide functional group to free acid, thereby reducing the molecule's biological activity. In this disclosure, derivatives of endocannabinoids at both the epoxide and the amide ends improve the biological properties of the compositions by reducing hydrolytic susceptibility in the body and increasing the longevity of the molecules. The synthesis of these derivatives is based on rational design to reduce the hydrolytic susceptibility of these groups to sEH and FAAH. Furthermore, these derivatives retain anti-inflammatory, anti-cancer, anti-platelet aggregatory and anti-angiogenic properties. By improving the biological stability, these compounds are better candidates for therapeutics. These molecules are derivatives of endogenous biological molecules found in all the tissues and are expected to have fewer side effects as compared to other typical anti-inflammatory drugs. Additionally since they target multiple signaling pathways leading to different varied effects, they are more likely to provide synergistic effects in disease conditions. For instance, as they are anti-neuroinflammatory and vasodilatory, they are expected to play important role in cerebrovascular diseases.

1. DEFINITIONS

As described herein, compounds of the invention can optionally be substituted with one or more substituents, such as are illustrated generally above, or as exemplified by particular classes, subclasses, and species of the invention. As described herein, the variables in formula I encompass specific groups, such as, for example, alkyl and cycloalkyl. As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise defined, all technical and scientific terms used herein have the same meaning as commonly understood by one of ordinary skill in the art. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "alkyl" as used herein, means a straight or branched chain saturated hydrocarbon. Representative examples of alkyl include, but are not limited to, methyl, ethyl, npropyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene," as used herein, means a divalent group derived from a straight or branched chain saturated hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and CH$_2$CH(CH$_3$)CH(CH$_3$)CH$_2$—.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "cyano" as used herein, represents a group of formula —CN.

The term "cycloalkyl" as used herein, means a monovalent group derived from an all-carbon non-aromatic ring system containing zero heteroatoms as ring atoms, and zero double bonds. The all-carbon ring system can be a monocyclic, bicylic, or tricyclic ring system, and can be a fused ring system, a bridged ring system, or a spiro ring system, or combinations thereof. Examples of cycloalkyls include, but are not limited to, cyclopropyl, cyclobutyl, cyclopentyl, cyclohexyl, cycloheptyl, cyclooctyl, and

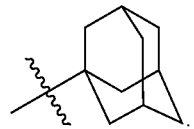 [SMILES: *C12CC3CC(CC(C3)C1)C2]

The cycloalkyl groups described herein can be appended to the parent molecular moiety through any substitutable carbon atom.

The term "cycloalkenyl" as used herein, means a monovalent group derived from an all-carbon non-aromatic ring system containing zero heteroatoms as ring atoms, and at least one carbon-carbon double bond. The cycloalkenyl may have from 5-10 carbon atoms as ring atoms. The cycloalkenyl may be monocyclic, bicyclic, bridged, fused, or spirocyclic. Exemplary monocyclic cycloalkenyl rings include cyclopentenyl, cyclohexenyl, cycloheptenyl, and bicyclo[2.2.1]heptenyl.

The term "halogen" means a chlorine, bromine, iodine, or fluorine atom.

The term "haloalkyl," as used herein, means an alkyl group, as defined herein, in which one, two, three, four, five, six, seven or eight hydrogen atoms are replaced by a halogen.

The term "heteroaryl," as used herein, means an aromatic heterocycle, i.e., an aromatic ring that contains at least one heteroatom selected from O, N, or S. A heteroaryl may contain from 5 to 12 ring atoms. A heteroaryl may be a 5- to 6-membered monocyclic heteroaryl or an 8- to 12-membered bicyclic heteroaryl. A 5-membered monocyclic heteroaryl ring contains two double bonds, and one, two, three, or four heteroatoms as ring atoms. Representative examples of 5-membered monocyclic heteroaryls include, but are not limited to, furanyl, imidazolyl, isoxazolyl, isothiazolyl, oxadiazolyl, oxazolyl, pyrazolyl, pyrrolyl, tetrazolyl, thiadiazolyl, thiazolyl, thienyl, and triazolyl. A 6-membered heteroaryl ring contains three double bonds, and one, two, three or four heteroatoms as ring atoms. Representative examples of 6-membered monocyclic heteroaryls include, but are not limited to, pyridinyl, pyridazinyl, pyrimidinyl, pyrazinyl, and triazinyl. The bicyclic heteroaryl is an 8- to 12-membered ring system having a monocyclic heteroaryl fused to an aromatic, saturated, or partially saturated carbocyclic ring, or fused to a second monocyclic heteroaryl ring. Representative examples of bicyclic heteroaryl include, but are not limited to, benzofuranyl, benzoxadiazolyl, 1,3-benzothiazolyl, benzimidazolyl, benzothienyl, indolyl, indazolyl, isoquinolinyl, naphthyridinyl, oxazolopyridine, quinolinyl, thienopyridinyl, 5,6,7,8-tetrahydroquinolinyl, and 6,7-dihydro-5H-cyclopenta[b]pyridinyl. The heteroaryl groups are connected to the parent molecular moiety through any substitutable carbon atom or any substitutable nitrogen atom contained within the groups.

The terms "heterocycle" or "heterocyclic" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic heterocycle, a fused bicyclic heterocycle, or a spiro heterocycle. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4-, 5-, 6-, 7-, or 8-membered monocyclic heterocycle ring wherein two of the substituents on the same carbon atom form a second ring having 3, 4, 5, 6, 7, or 8 members. Examples of a spiro heterocycle include, but are not limited to, 1,4-dioxa-8-azaspiro[4.5]decanyl, 2-oxa-7-azaspiro[3,5]nonanyl, 2-oxa-6-azaspiro[3.3]heptanyl, and 8-azaspiro[4.5]decane. The monocyclic heterocycle groups of the present invention may contain an alkylene bridge of 1, 2, or 3 carbon atoms, linking two nonadjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic fused bicyclic, and spiro heterocycle groups are connected to the parent molecular moiety through any substitutable carbon atom or any substitutable nitrogen atom contained within the group.

The term "hydroxy" as used herein, means an —OH group.

Terms such as "alkyl," "cycloalkyl," "alkylene," etc. as used herein may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

If a group is described as being "substituted", a non-hydrogen substituent group is in the place of hydrogen radical on a carbon or nitrogen of that group. Thus, for example, a substituted alkyl is an alkyl in which at least one non-hydrogen radical is in the place of a hydrogen radical on the alkyl. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated). Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfonyl, —COOH, ketone, amide, carbamate, and acyl.

When a group is referred to as "unsubstituted" or not referred to as "substituted" or "optionally substituted", it means that the group does not have any substituents. If a group is described as being "optionally substituted", the group may be either (1) not substituted or (2) substituted. If a group is described as being optionally substituted with up to a particular number of non-hydrogen radicals, that group may be either (1) not substituted; or (2) substituted by up to that particular number of substituent groups or by up to the maximum number of substitutable positions on that group, whichever is less.

If substituents are described as being independently selected from a group, each substituent is selected independent of the other. Each substituent, therefore, may be identical to or different from the other substituent(s).

Unless otherwise stated, structures depicted herein are also meant to include all isomeric (e.g., enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I. The structures also include zwitterionic forms of the compounds or salts of formula I where appropriate.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, "treat," "treating" and the like means a slowing, stopping or reversing of progression of cancer when provided a composition described herein to an appropriate control subject. The term also means a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

As used herein, "subject" or "patient" means an individual having symptoms of, or at risk for, cancer, increased inflammation, increased platelet aggregation, increased angiogenesis, or other disease or disorder. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

2. COMPOUNDS

In one aspect, the present disclosure provides compounds or compositions of formula (I), or a pharmaceutically acceptable salt thereof,

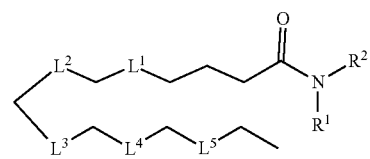

wherein, one of $L^1$, $L^2$, $L^3$, $L^4$, and $L^5$ is

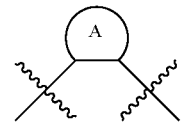

and the others of $L^1$, $L^2$, $L^3$, $L^4$, and $L^5$ are

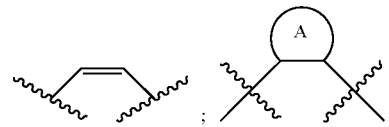

is 3- to 6-membered ring containing at least one heteroatom selected from the group consisting of oxygen, nitrogen, and sulfur;

$R^1$ is hydrogen, $C_{1-6}$alkyl, $C_{1-6}$haloalkyl, —$C_{1-6}$alkylene-$R^{x1}$, -$G^1$, or —$C_{1-6}$alkylene-$G^1$;

$G^1$ is $C_{3-8}$cycloalkyl, $C_{3-8}$cycloalkenyl, aryl, heteroaryl, or heterocycle, wherein $G^1$ is optionally substituted with 1, 2, 3, or 4 $R^{x1}$;

$R^2$ is $C_{1-6}$alkyl, $C_{1-6}$haloalkyl, —$C_{1-6}$alkylene-$R^{x2}$, -$G^2$, or —$C_{1-6}$alkylene-$G^2$;

$G^2$ is $C_{3-8}$cycloalkyl, $C_{3-8}$cycloalkenyl, acyl, heteroaryl, or heterocycle, wherein $G^2$ is optionally substituted with 1, 2, 3, or 4 $R^{x2}$;

$R^{x1}$ and $R^{x2}$ at each occurrence are independently cyano, —OH, —O$C_{1-4}$alkyl, —OC(O)$C_{1-4}$alkyl, —$NH_2$, —NH$C_{1-4}$alkyl, —N($C_{1-4}$alkyl)$_2$, —NHC(O)$C_{1-4}$alkyl, or —N($C_{1-4}$alkyl)C(O)$C_{1-4}$alkyl;

provided that $R^2$ is not —$CH_2CH_2OH$ when

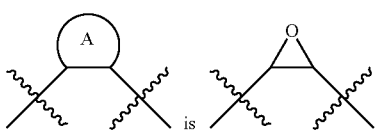

In some embodiments, $L^1$ is

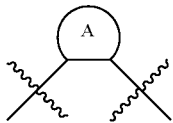

and $L^2$, $L^3$, $L^4$, and $L^5$ are

, i.e., compounds of formula (I) have formula (I-a).

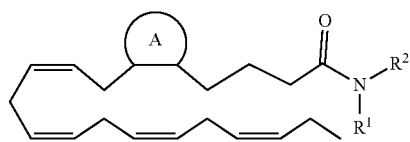
(I-a)

In some embodiments, compounds of formula (I-a) have formula (I-aa), wherein X is O, NH, or S.

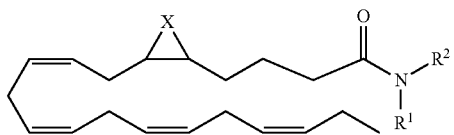
(I-aa)

In some embodiments, $L^2$ is

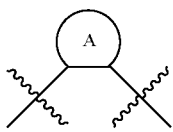

and $L^1$, $L^3$, $L^4$, and $L^5$ are

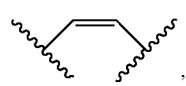 [SMILES: */C=C\*], i.e., compounds of formula (I) have formula (I-b).

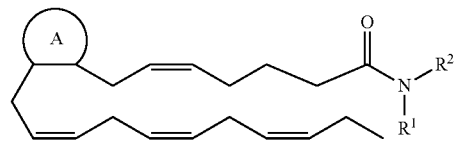
(I-b)

In some embodiments, compounds of formula (I-b) have formula (I-ba), wherein X is O, NH, or S.

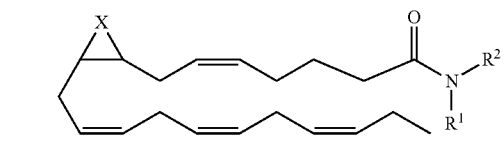
(I-ba)

In some embodiments, $L^3$ is

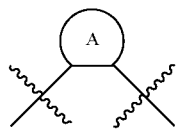

and $L^1$, $L^2$, $L^4$, and $L^5$ are

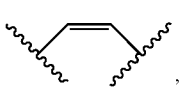, i.e., compounds of formula (I) have formula (I-c).

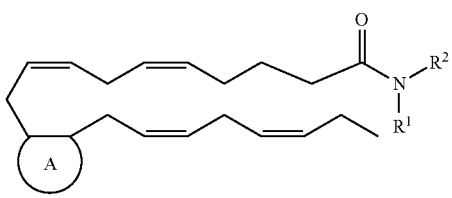
(I-c)

In some embodiments, compounds of formula (I-c) have formula (I-ca), wherein X is O, NH, or S.

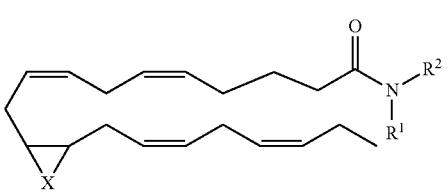
(I-ca)

In some embodiments, $L^4$ is

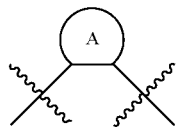

and $L^1$, $L^2$, and $L^5$ are

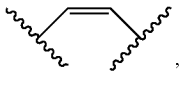, i.e., compounds of formula (I) have formula (I-d).

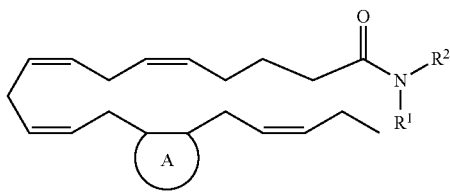

(I-d)

In some embodiments, compounds of formula (I-d) have formula (I-da), wherein X is O, NH, or S.

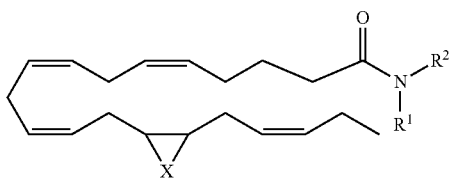

(I-da)

In some embodiments, $L^5$ is

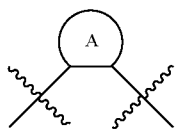

and $L^1$, $L^2$, $L^3$, and $L^4$ are

i.e., compounds of formula (I) have formula (I-e).

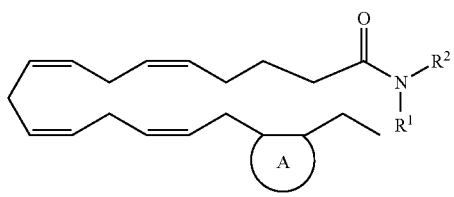

(I-e)

In some embodiments, compounds of formula (I-e) have formula (I-ea), wherein X is O, NH, or S.

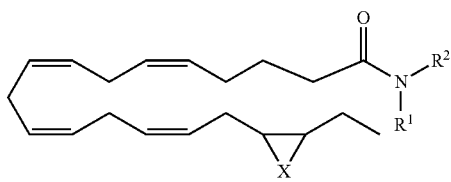

(I-ea)

In some embodiments,

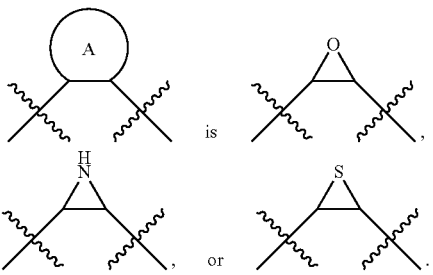

is

In some embodiments, $R^1$ is hydrogen, $C_{1-6}$alkyl (such as methyl or ethyl), or $C_{1-6}$haloalkyl (such as chloromethyl or chloroethyl). In some embodiments, $R^1$ is hydrogen. In some embodiments,

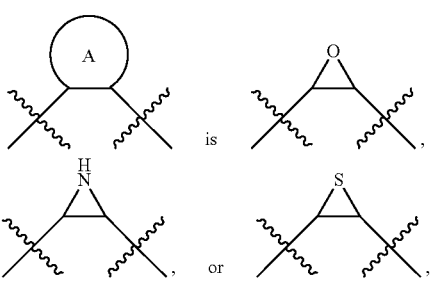

is and $R^1$ is hydrogen.

In some embodiments, $R^2$ is $C_{1-6}$alkyl, —$C_{1-6}$alkylene-$R^{x2}$, -$G^2$, or —$C_{1-6}$alkylene-$G^2$. For example, $R^2$ may be $C_{1-6}$alkyl, such as n-butyl, sec-butyl, isobutyl, tert-butyl, n-pentyl, isopentyl, neopentyl, or n-hexyl. For example, $R^2$ may be —$C_{1-6}$alkylene-$R^{x2}$, such as —$CH_2CH_2$—$R^{x2}$, —$CH_2CH_2CH_2$—$R^{x2}$, or —$CH(CH_3)CH_2$—$R^{x2}$. For example, $R^2$ may be -$G^2$ or —$C_{1-6}$alkylene-$G^2$, and $G^2$ is $C_{3-8}$cycloalkyl, $C_{3-8}$cycloalkenyl, aryl, heteroaryl, or heterocycle, wherein $G^2$ is optionally substituted with 1, 2, 3, or 4 $R^{x2}$.

In some embodiments, $G^1$ or $G^2$ is a $C_{3-8}$cycloalkyl optionally substituted with 1, 2, 3, or 4 $R^{x2}$. For example, $G^1$ or $G^2$ may be

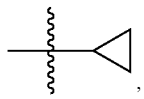

which is optionally substituted with 1, 2, or 3 $R^{x2}$. In some embodiments, $R^2$ is -$G^2$ or —$C_{1-6}$alkylene-$G^2$, and $G^2$ is a $C_{3-8}$cycloalkyl optionally substituted with 1, 2, 3, or 4 $R^{x2}$. In some embodiments, $R^2$ is -$G^2$ or —$C_{1-6}$alkylene-$G^2$, and $G^2$ is

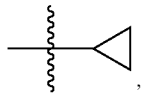

which is optionally substituted with 1, 2, or 3 $R^{x2}$.

In some embodiments, $R^{x1}$ and $R^{x2}$ at each occurrence are independently —OH, —$OC_{1-4}$alkyl, —$OC(O)C_{1-4}$alkyl, —NH$_2$, —NHC$_{1-4}$alkyl, or —N(C$_{1-4}$alkyl)$_2$. In some embodiments, R$^{x2}$ at each occurrence is independently —OH or —NH$_2$. For example, R$^2$ may be —C$_{1-6}$alkylene-OH (such as —CH$_2$CH$_2$CH$_2$—OH, or —CH(CH$_3$)CH$_2$—OH) or —C$_{1-6}$alkylene-NH$_2$. For example, R$^2$ may be -G$^2$ or —C$_{1-6}$alkylene-G$^2$, wherein G$^2$ is a C$_{3-8}$cycloalkyl, C$_{3-8}$cycloalkenyl, aryl, heteroaryl, or heterocycle as defined herein, wherein G$^2$ is optionally substituted with 1, 2, 3, or 4 R$^{x2}$, and wherein R$^{x2}$ at each occurrence is independently —OH or —NH$_2$. In some embodiments, R$^2$ is

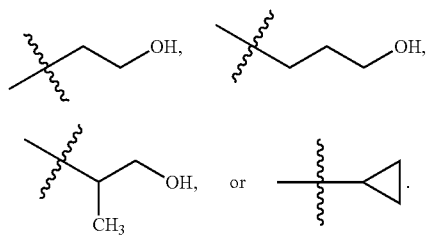

In some embodiments,

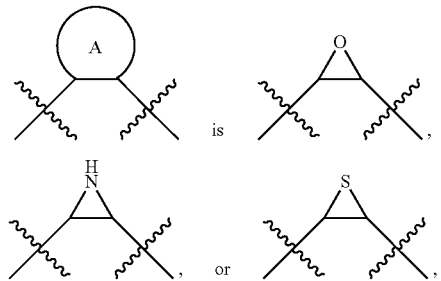

R$^1$ is hydrogen, and R$^2$ is C$_{1-6}$alkyl.

In some embodiments,

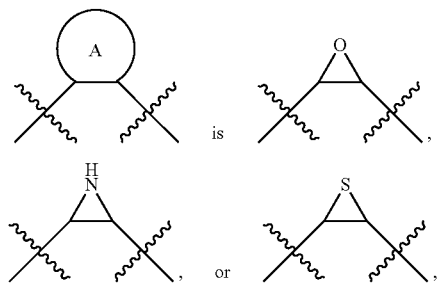

R$^1$ is hydrogen, and R$^2$ is —C$_{1-6}$alkylene-R$^{x2}$ as described herein. In some embodiments,

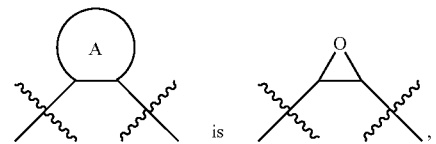

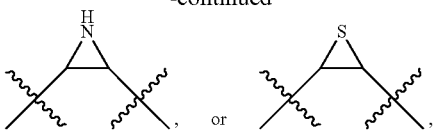

R$^1$ is hydrogen, and R$^2$ is —C$_{1-6}$alkylene-OH (such as

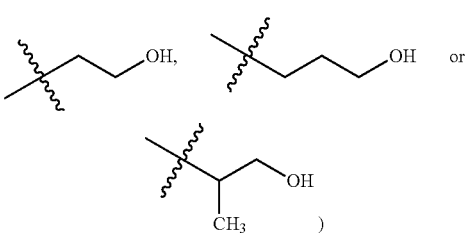

or —C$_{1-6}$alkylene-NH$_2$.

In some embodiments,

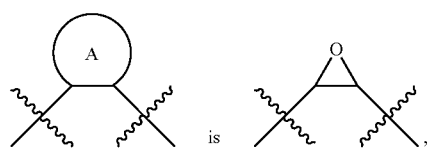

R$^1$ is hydrogen, R$^2$ is —C$_{1-6}$alkylene-OH. In some embodiments,

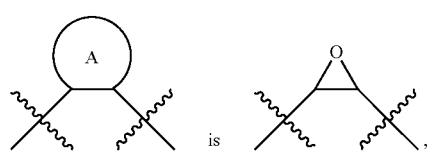

R$^1$ is hydrogen, R$^2$ is —C$_{1-6}$alkylene-OH. In some embodiments,

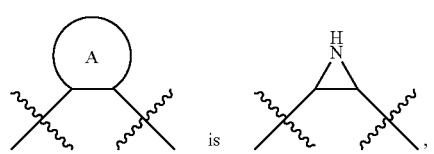

R$^1$ is hydrogen, R$^2$ is —C$_{1-6}$alkylene-OH. In some embodiments,

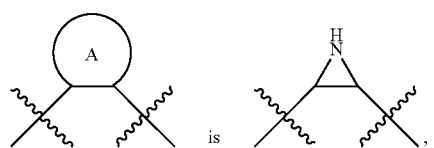

R$^1$ is hydrogen, R$^2$ is —C$_{1-6}$alkylene-NH$_2$. In some embodiments,

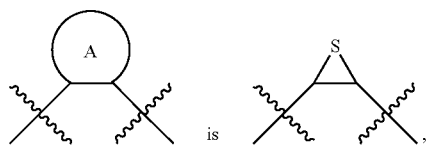

$R^1$ is hydrogen, $R^2$ is —$C_{1-6}$alkylene-OH. In some embodiments,

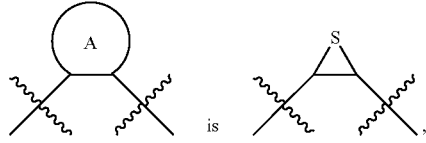

$R^1$ is hydrogen, $R^2$ is —$C_{1-6}$alkylene-NH$_2$.

In some embodiments,

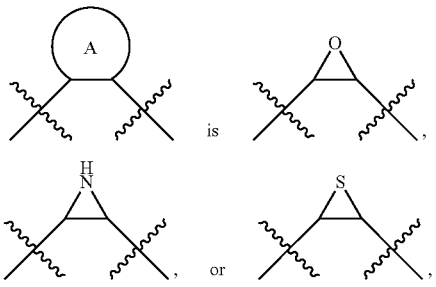

$R^1$ is hydrogen, and $R^2$ is -$G^2$ or —$C_{1-6}$alkylene-$G^2$, in which $G^2$ and $R^{x2}$ are as described herein. In some embodiments,

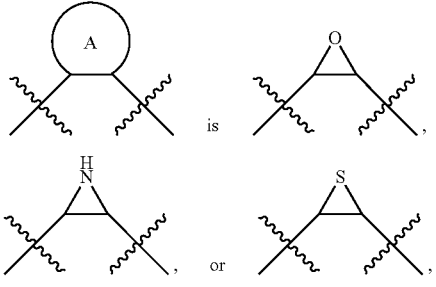

$R^1$ is hydrogen, $R^2$ is -$G^2$ or —$C_{1-6}$alkylene-$G^2$, and $G^2$ is a $C_{3-8}$cycloalkyl optionally substituted with 1, 2, 3, or 4 $R^{x2}$. In some embodiments,

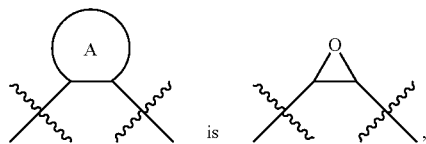

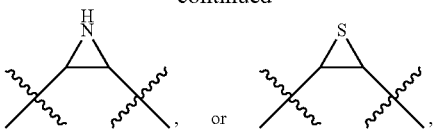

$R^1$ is hydrogen, $R^2$ is -$G^2$ or —$C_{1-6}$alkylene-$G^2$, $G^2$ is a $C_{3-8}$cycloalkyl optionally substituted with 1, 2, 3, or 4 $R^{x2}$, and $R^{x2}$ at each occurrence is independently —OH or —NH$_2$.

In some embodiments,

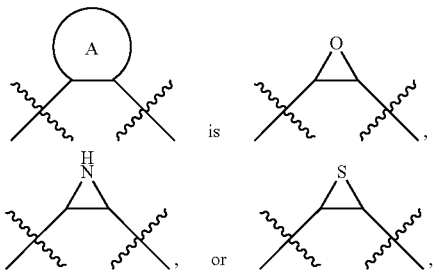

$R^1$ is hydrogen, $R^2$ is -$G^2$ or —$C_{1-6}$alkylene-$G^2$, and $G^2$ is

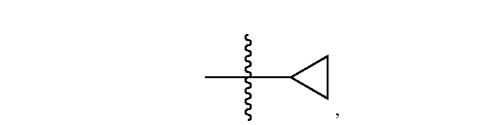

wherein G2 is unsubstituted or substituted with 1 or 2 $R^{x2}$, $R^{x2}$ at each occurrence being independently —OH or —NH$_2$.

In some embodiments,

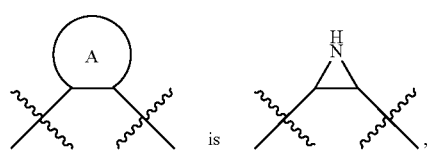

$R^1$ is hydrogen, $R^2$ is

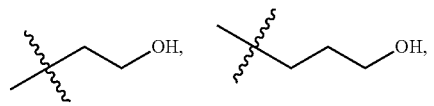

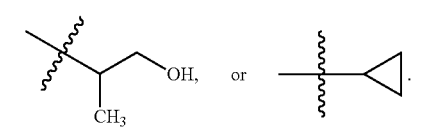

In some embodiments,

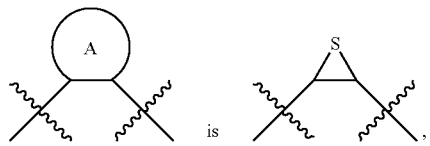

$R^1$ is hydrogen, $R^1$ is

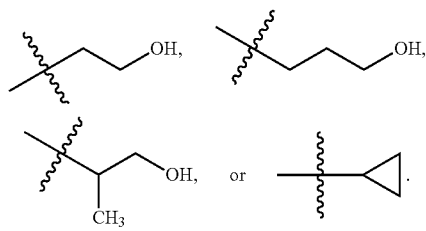

In some embodiments,

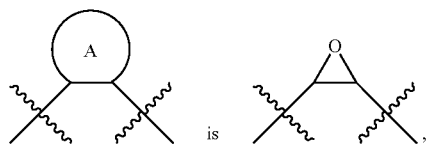

$R^1$ is hydrogen, $R^2$ is

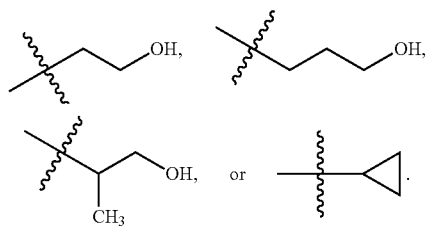

In some embodiments, the compound of formula (I) is selected from the group consisting of

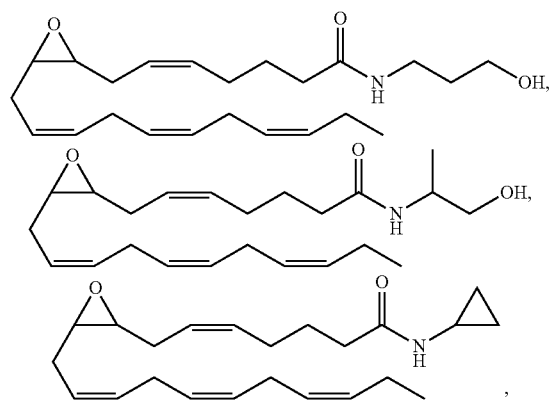

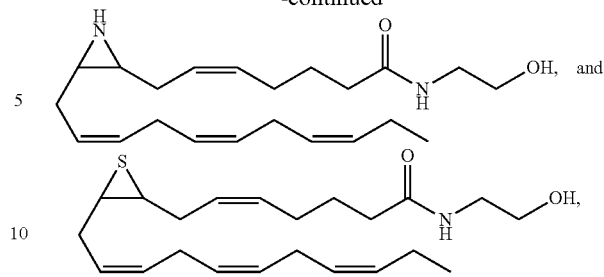

or a pharmaceutically acceptable salt thereof.

Figure 1B:
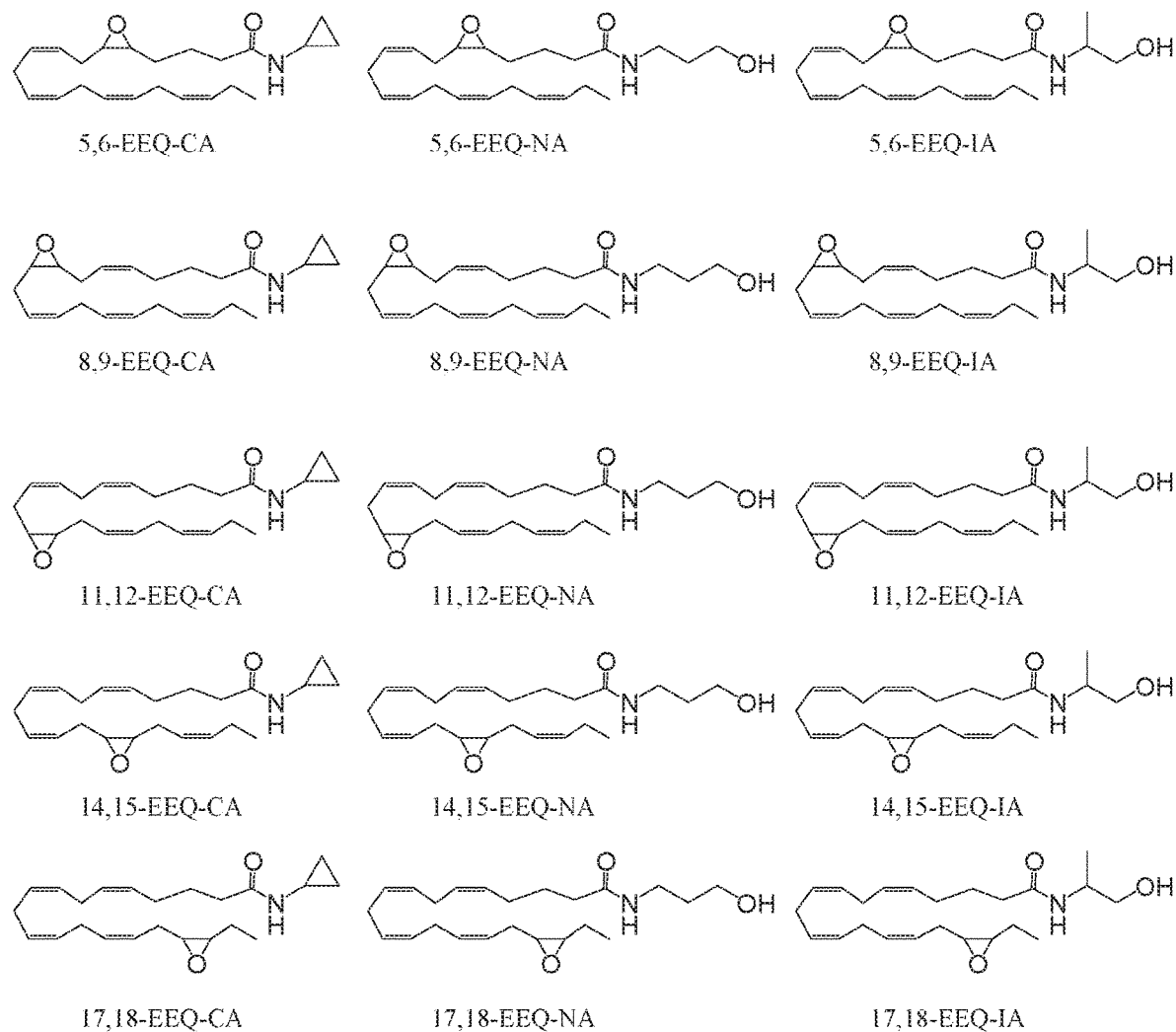
FIG. 1B shows modifications at the carboxylic acid group of EEQ-EA for all corresponding epoxide derivatives, i.e. 5,6-EEQ-cyclopropylamine, 5,6-EEQ-n-propylamine, 5,6-EEQ-isopropylamide through to 17-18-EEQ-cyclopropylamine, 17,18-EEQ-n-propylamine, 17,18-EEQ-isopropylamide.
Figure 1C:
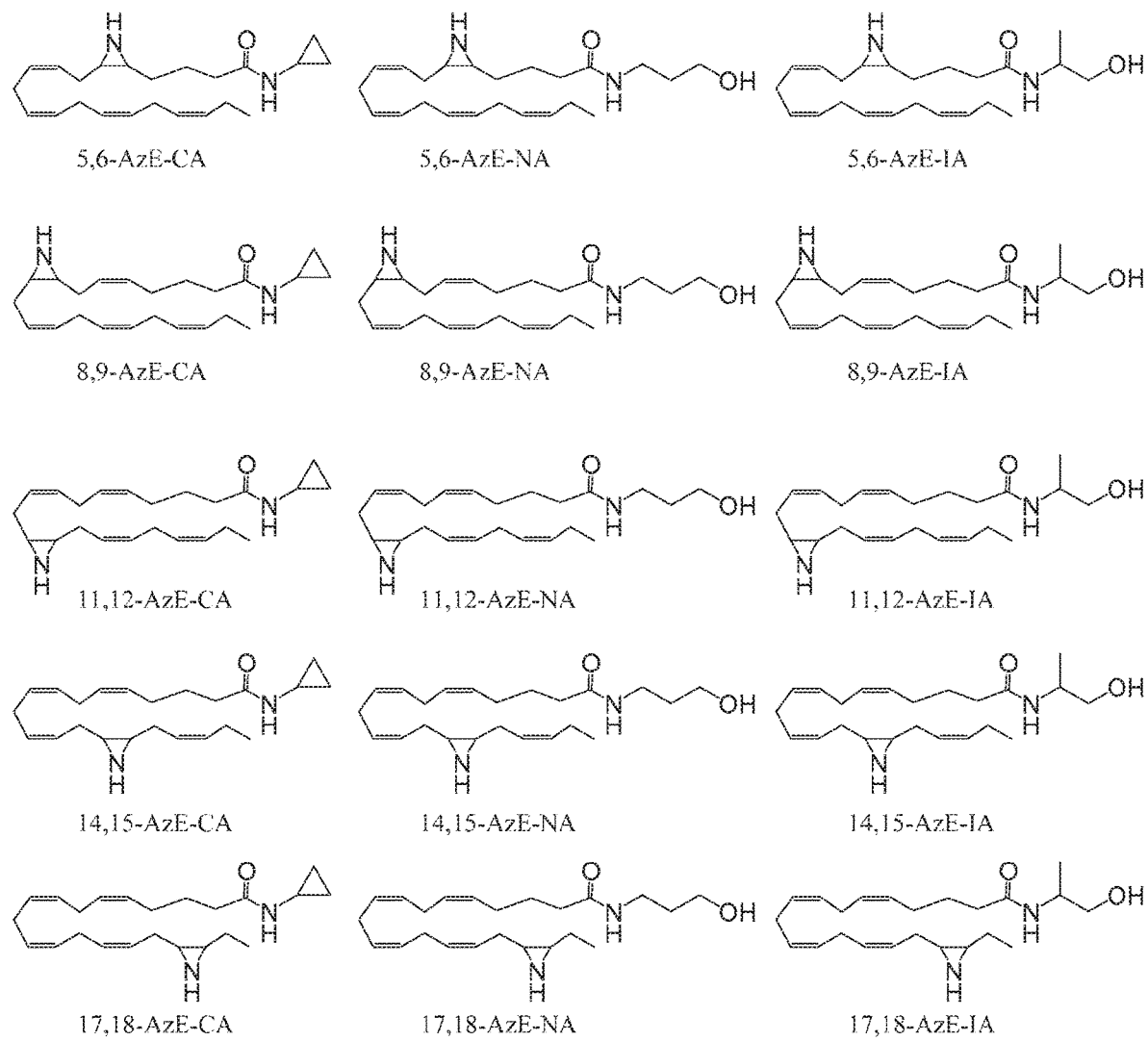
FIG. 1C shows aziridine derivatives of 5,6-EEQ through 17,18-EEQ for three amide groups.
Figure 1D:
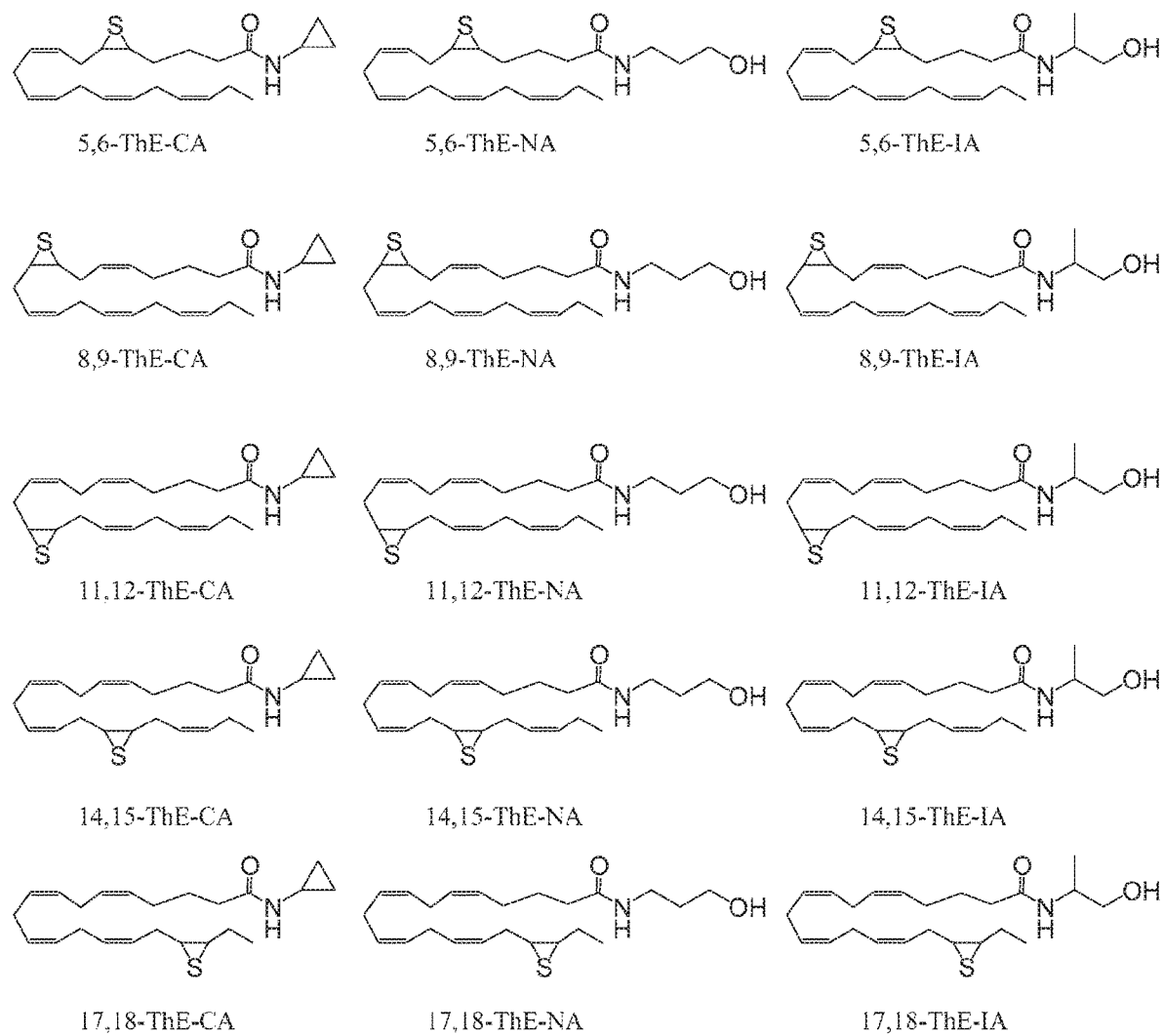
FIG. 1D shows thiirane derivatives of 5,6-EEQ through 17,18-EEQ for three amide groups.

In some embodiments, the compound of formula (I) is a compound shown in FIG. 1B, 1C, and/or 1D.

Also provided herein is a composition comprising the structure (i):

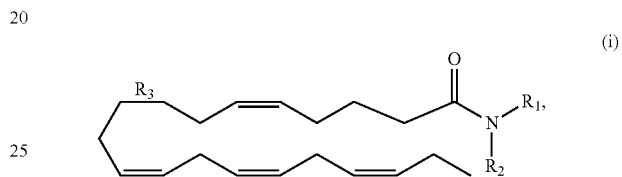

wherein,
R1 and R2 is selected from

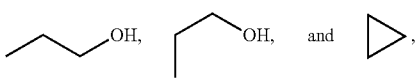

carbon chain with an n=3, 4, 5 or 6 ending in CH3, —OH, or —NH2, saturated cyclic rings with 3, 4, 5 or 6 carbons with no substitutions, saturated cyclic rings with 3, 4, 5 or 6 carbons with substitutions of —OH and —NH2, unsaturated cyclic rings with 3, 4, 5 or 6 carbons with no substitutions, unsaturated cyclic rings with 3, 4, 5 or 6 carbons with substitutions of —OH and —NH2, aromatic groups with no substitutions, aromatic groups with substitutions of —OH or —NH2, and saturated or unsaturated cyclic rings containing N, O or S, and
R3 is selected from 3, 4, 5 or 6 membered rings containing oxygen, nitrogen or sulfur.

In some embodiments, the composition is selected from the group consisting of

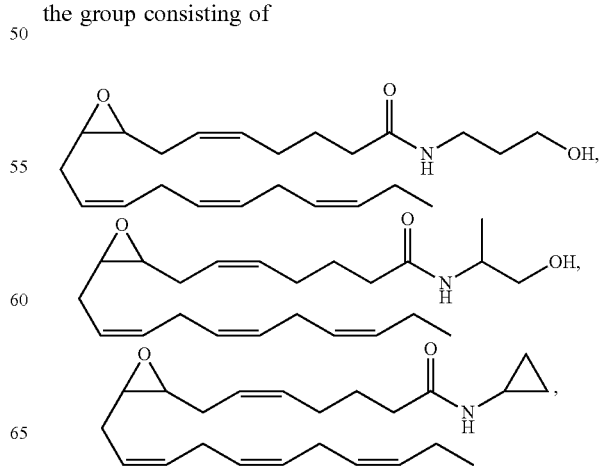

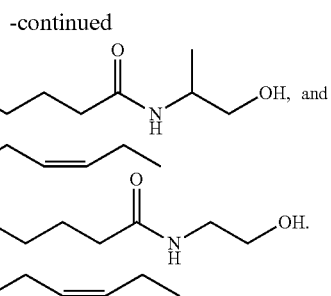

A compound described herein can be in the form of a salt, e.g., a pharmaceutically acceptable salt. As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N(C$_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl (e.g., phenyl/substituted phenyl) sulfonate.

The compounds or compositions disclosed herein may include isotope-labelled forms. An isotope-labelled form of a compound is identical to the compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound by well-known methods include isotopes of hydrogen, carbon, nitrogen, oxygen, fluorine and chlorine, for example 2H, 3H, 13C, 14C, 15N, 18O, 17O, 18F and 36Cl.

3. PHARMACEUTICAL COMPOSITIONS

In another aspect, the present disclosure provides a pharmaceutical composition are provided, which comprises a compound as described herein or a pharmaceutically acceptable salt thereof, and optionally a pharmaceutically acceptable carrier, adjuvant or vehicle. In certain embodiments, these pharmaceutical compositions optionally further comprise one or more additional therapeutic agents. In one embodiment, the pharmaceutical composition comprises a therapeutically effective amount of a compound as described herein, or a pharmaceutically acceptable salt thereof, and one or more pharmaceutically acceptable carriers or vehicles.

Pharmaceutical compositions of the present invention may be manufactured by processes well known in the art. e.g., by means of conventional mixing, dissolving, granulating, dragee-making, levigating, emulsifying, encapsulating, entrapping or lyophilizing processes.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N(C$_{1-4}$alkyl)4 salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl (e.g., phenyl/substituted phenyl) sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the disease being treated.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, cement, putty, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type may also be employed as fillers in soft and hardfilled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or trans dermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds described herein can be administered as a pharmaceutical composition comprising the compounds of interest in combination with one or more pharmaceutically acceptable carriers. The phrase "therapeutically effective amount" of the present compounds means sufficient amounts of the compounds to treat disorders, at a reasonable benefit/risk ratio applicable to any medical treatment. It is understood, however, that the total daily dosage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the all to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer.

The compositions described herein may be administered with additional compositions to prolong stability, delivery, and/or activity of the compositions, or combined with additional therapeutic agents, or provided before or after the administration of additional therapeutic agents.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

4. METHODS OF USE

The endocannabinoid system is involved in a broad range of functions and is implicated in a variety of physiological and pathological conditions (inflammation, immunomodulation, analgesia, cancer and others) as described in Bifulco et al. (2007) Oncol Rep 17:813-816. The compounds or compositions as disclosed herein, or pharmaceutically acceptable salts thereof, or pharmaceutical compositions as described herein, may be used for treating a disease, condition, or disorder in a subject. For example, the compounds or compositions disclosed herein may be used for treating cancer, reducing inflammation, reducing platelet aggregation, reducing angiogenesis, or inducing vasoconstriction or vasodilation.

Cancer

Provided are uses of the compounds or compositions for treating cancer. Also provided are uses of the compounds or compositions in the manufacture of a medicament for treating cancer. The disclosed compounds and compositions may be used in methods of treating cancer, comprising administering to a subject in need thereof a therapeutically effective amount of a compound of formula (I), or a pharmaceutically acceptable salt or pharmaceutical composition thereof.

Cancer is a class of diseases which occurs because cells become immortalized; they fail to heed customary signals to turn off growth which is a normal function of remodeling in the body that requires cells to die on cue. Apoptosis, or programmed cell death, can become defective and when this happens malignant transformation can take place. The immortalized cells grow beyond their normal limits and invade adjacent tissues. The malignant cells may also metastasize and spread to other locations in the body via the bloodstream or lymphatic system. Cancer cells often form a mass known as a tumor.

Compounds of the present invention have functionalities that may be advantageous for cancer treatment including inhibition of cell proliferation and induction of apoptosis. As a class of molecules, endocannabinoids and cannabinoids show anti-tumor effects in various tumor cells, such as, e.g. neuroblastoma, mantle cell lymphoma, colon cancer, osteosarcoma, and glioma. Activation of the two cannabinoid receptors, CB1 and CB2, can lead to the inhibition of cell proliferation and induction of apoptosis in multiple types of cancer cell lines resulting in the reduction of tumor growth in vivo.

The methods can be used with any cancer cell or in a subject having any type of cancer, for example those described by the National Cancer Institute. The cancer may be a carcinoma, sarcoma, lymphoma, leukemia, melanoma, mesothelioma, multiple myeloma, or seminoma. In some embodiments, the cancer is an osteosarcoma. The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus.

There are many different treatment options for cancer and the treatment sought is often determined by the type and stage of the cancer. Treatment options include; chemotherapeutic drug treatment, hormonal drug treatment, radiotherapy, surgery, complementary therapies and combinations thereof. The compounds and compositions of the present invention may be used in combination with any well-known cancer treatment options.

Reducing Inflammation

By virtue of the anti-inflammatory properties shown herein, the compounds and compositions according to the present invention may be useful in a wide variety of indications having an inflammatory or autoimmune mechanism involved in their etiology or pathogenesis. Manipulation and use of endocannabinoids in vivo has been shown to be a potent treatment against inflammatory disorders.

Provided herein are uses of the compounds or compositions for reducing inflammation in a subject. Also provided herein are uses of the compounds or compositions in the manufacture of a medicament for reducing inflammation in a subject. The disclosed compounds and compositions may be used in various methods including methods of reducing inflammation, comprising administering to a subject in need thereof a therapeutically effective amount of a compound of formula (I), or a pharmaceutically acceptable salt or pharmaceutical composition thereof.

Inflammatory disorders underlie a vast variety of human diseases. The immune system is often involved with inflammatory disorders, demonstrated in both allergic reactions and some myopathies, with many immune system disorders resulting in abnormal inflammation. Compounds of the present invention may be used to reduce inflammation in a subject suffering from many acute and chronic diseases/disorders that are inflammatory in their nature including but not limited to rheumatoid diseases e.g. rheumatoid arthritis, osteoarthritis, diseases of the visceral system e.g. inflammatory bowel syndrome, ulcerative colitis, and Crohn's Disease, autoimmune diseases, e.g. lupus erythematodes, lung diseases like asthma and COPD, Alzheimer's disease, cancer, multiple sclerosis, Psoriasis, sarcoidosis, and spondyloarthropathy (erg. ankylosing spondylitis).

Reduction in Platelet Aggregation

Provided herein are uses of the compounds or compositions for reducing platelet aggregation in a subject. Also provided herein are uses of the compounds or compositions in the manufacture of a medicament for reducing platelet aggregation in a subject. The disclosed compounds and compositions may be used in various methods including methods of reducing platelet aggregation, comprising administering to a subject in need thereof a therapeutically effective amount of a compound of formula (I), or a pharmaceutically acceptable salt or pharmaceutical composition thereof.

Platelets are small disc-shaped blood cells and their chief function is to maintain the integrity of the vascular system; not only during injury, but also day-to-day wear and tear. To do this, platelets can, when they come into contact with certain materials and chemicals undergo a process known as the aggregation-adhesion reaction. When they aggregate platelets change from their discoid shape to a more spherical form, they throw out long processes known as pseudopodia and somehow become sticky. The result of this is that they stick to one another and to the damaged tissue, thus plugging gaps or holes in the blood vessel wall. Endocannabinoids may control platelet activation and limit aggregate formation.

The phenomenon of aggregation is the most widely studied property of platelets: it is of interest not only for scientific reasons (platelets make an ideal test system for examining cellular mechanisms and drug action), but also has diagnostic significance since there are many conditions in which platelet function is abnormal.

The compounds or compositions as disclosed herein may be used to reduce platelet aggregation in a subject suffering from many vaso-occlusive disorders such as unstable angina, acute myocardial infarction, reocclusion of vessels following balloon angioplasty, transient ischemic attacks and strokes. Thrombocytosis or increased platelet count may occur in certain disease states such as cancer, chronic infections, and certain blood diseases, and may cause increased blood clot formation or thrombosis due to platelet aggregation. The compounds of the present invention may be used to reduce platelet aggregation in various other diseases involving thrombosis, such as venous thrombosis, established peripheral arterial disease, thrombophlebitis, arterial embolism, coronary and cerebral arterial thrombosis, unstable angina, myocardial infarction, stroke, cerebral embolism, renal embolism, pulmonary embolism and other embolism- or thrombosis-related afflictions produced by but not limited to procedural or surgical interventions. Such conditions may also result from thromboembolism and reocculsion during and after thermbolytid therapy, after angioplasty, and after coronary artery bypass.

The compounds or compositions as disclosed herein may be used to induce platelet aggregation in a subject suffering from various blood coagulation disorders including, but not limited to, hemostatic disorders characterized by prolonged bleeding times, thrombocytopenias, von Willebrand disease, hemophilia, myeloproliferative disorders (MPDs), myelodysplasia, paraproteinemias, and uremia. In particular, conditions can be treated which are caused by an impaired aggregation behavior of blood platelets or thrombopathies, and bleeding conditions caused by platelets deficiency (thrombocytopenia).

Anti-Angiogenic

Angiogenesis is an important biological process, necessary for reproduction, development, and wound repair. Angiogenesis begins with the degradation of the basement membrane by proteases secreted from activated endothelial cells. In adults, the rate of proliferation of endothelial cells is generally low, and tissues are normally in a state of angiogenesis equilibrium in which growth factors that simulate new vessel growth are balanced by other factors which inhibit vessel growth. However, rapid proliferation of endothelial cells can occur during certain processes such as reproduction and wound healing. The rate of angiogenesis responds to a change in the levels of angiogenic growth factors.

Abnormal angiogenesis can occur in various diseases and disorders. These diseases and disorders can be divided into two groups: diseases involving excessive angiogenesis, and diseases involving insufficient angiogenesis. In some diseases, decreased angiogenesis is beneficial due to abnormal angiogenesis evidenced by the formation of abnormal blood vessels, which are heterogeneous with regard to organization, unevenly distributed, and chaotic. Abnormal blood vessels generally exhibit a serpentine or tortuous course, branch irregularly and form arterio-venous shunts, and may also be thin-walled and leaky. It is therefore desirable to be able to modulate the rate of angiogenesis in order to help prevent or treat these types of conditions, either by increasing or decreasing the rate of angiogenesis.

The compounds or compositions as disclosed herein may reduce cell migration and proliferation and are thus useful in the treatment of diseases with overactive cell migration and proliferation, such as disorders involving excessive angiogenesis. Provided herein are uses of the compounds or compositions for reducing angiogensis in a subject. Also provided are uses of the compounds or compositions in the manufacture of a medicament for reducing angiogenesis in a subject. The disclosed compounds and compositions may be used in various methods including methods of reducing angiogenesis, comprising administering to a subject in need thereof a therapeutically effective amount of a compound of formula (I), or a pharmaceutically acceptable salt or pharmaceutical composition thereof.

The compounds or compositions as disclosed herein may be used for treating diseases and disorders involving excessive angiogenesis, abnormal angiogenesis, or where decreased angiogenesis would be beneficial, include retinal neovascularization, hemangioma solid tumors, metastasis, psoriasis, neovascular glaucoma, diabetic retinopathy, macular degeneration, arthritis (e.g., rheumatoid arthritis), endometriosis, retinopathy of prematurity (ROP), gingivitis, and pre-eclampsia.

Prevention of solid tumor growth is of particular interest. Examples of cancers that typically involve solid tumor growth include neoplasms of the central nervous system such as, but again not necessarily limited to glioblastomas, astrocytomas, neuroblastomas, meningiomas, ependymomas, cancers of hormone-dependent tissues such as prostate, testicles, uterus, cervix, ovary, mammary carcinomas including but not limited to carcinoma in situ, medullary carcinoma, tubular carcinoma, invasive (infiltrating) carcinomas and mucinous carcinomas; melanomas, including but not limited to cutaneous and ocular melanomas; cancers of the lung which at least include squamous cell carcinoma, spindle carcinoma, small cell carcinoma, adenocarcinoma and large cell carcinoma; and cancers of the gastrointestinal system such as esophageal, stomach, small intestine, colon, colorectal, rectal and anal region which at least include adenocarcinomas of the large bowel.

Vasoconstriction and Vasodilation

The compounds or compositions as disclosed herein may be used for inducing vasoconstriction or vasodilation in a subject. Also provided are uses of the compounds or compositions in the manufacture of a medicament for inducing vasoconstriction or vasodilation in a subject. The disclosed compounds or compositions as disclosed herein may be used in a method of inducing vasoconstriction or vasodilation, comprising administering to a subject in need thereof a therapeutically effective amount of a compound of formula (I), or a pharmaceutically acceptable salt or pharmaceutical composition thereof.

The compounds or compositions as disclosed herein may modulate blood flow through vasoconstriction and/or vasodilation. In some embodiments, the compounds or compositions may induce vasoconstriction. Vasoconstriction is the narrowing of the blood vessels resulting from contraction of the muscular wall of the vessels, in particular the large arteries and small arterioles. The process is particularly important in staunching hemorrhage and acute blood loss. The compounds and compositions described herein may be used to treat shock, migraines, low blood pressure, excess bleeding, and allergic reactions.

In some embodiments, the compounds or compositions as disclosed herein may induce vasodilation. Vasodilation is the widening of blood vessels to increase blood flow in the body to tissues that need it. The compounds and compositions as disclosed herein may be used to treat conditions such as hypertension, wherein the subject has an abnormally high blood pressure, as well as angina, congestive heart failure, and erectile dysfunction, diabetic nephropathy, Raynaud's syndrome, cardiomyopathy, and where maintaining a lower blood pressure reduces the subject's risk of developing other cardiac problems. The compounds and compositions as disclosed herein may be used prevent stroke, heart attacks, or heart failures.

5. EXAMPLES

General Synthesis of EEQ. A nonspecific epoxidation reaction with 50 mg of eicosapentaenoic acid (EPA) dissolved in 2 mL of dichloromethane (DCM) with 2 mol equiv of metachloroperoxybenzoic acid (mCPBA) was reacted for 1 h at room temperature. The reaction was stopped with an equal volume of 10% aqueous $NaHCO_3$ to remove mCPBA from the organic layer, and the aqueous layer was re-extracted thrice with equal volumes of DCM; the combined organic layer was dried in vacuo. Purification of regioisomers was achieved using normal-phase HPLC (NP-HPLC) using a Zorbax-$NH_2$ semipreparative column (5 μm, 9.4× 250 mm, Agilent, PN880952-208) with an isocratic gradient (hexane/isopropanol/acetic acid, 90:10:0.1) coupled to an HPLC system. For coeluting regioisomers of EPA-epoxides (17,18-EEQ and 11,12-EEQ), the mixtures were further purified on the same system using reverse-phase HPLC (RP-HPLC), a Sun Fire Prep C18 column (5 μm, 19×50 mm, PN 186002566; Waters), a mobile system composed of solvent A ($H_2O$/acetonitrile/acetic acid, 95:5:0.1) and solvent B ($H_2O$/acetonitrile/acetic acid, 5:95:0.1), and a linear gradient from 50 to 0% A in 50 min. The synthesis of 17,18-EEQ, 14,15-EEQ, 11,12-EEQ, 8,9-EEQ, and 5,6-EEQ was confirmed by comparing retention times relative to authentic standards purchased from Cayman Chemical and high-resolution mass spectrometry.

Example 1. Synthesis of EEQ-EA and Amino Terminal Derivatives

Scheme 1 shows a representative synthesis of amide modified 17,18-EEQ derivative. The purified epoxide isomer may be reacted with the respective amine in the presence of EDC and NHS to produce the coupled product with above 80% conversion in all cases. This process may also be applied to the synthesis of compounds having an epoxide at the 5, 6, 8, 9, 11, 12, or 14, 15 positions.

Scheme 1

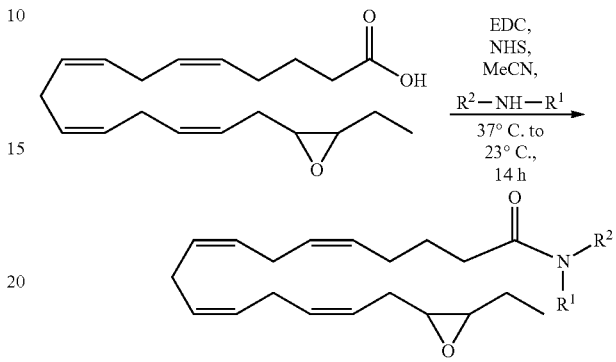

In a solution of epoxide in acetonitrile (MeCN), a solution of 1-Ethyl-3-(3-dimethylaminopropyl) carbodiimide (EDC) (10 mg/mL in acetonitrile) and N-hydroxysuccinimide (NHS) (10 mg/mL in acetonitrile) in the ratio of (1:40:40) is added and incubated at 37° C. for 20 mins. Next, a solution of amine (2 mg/mL in acetonitrile) in the ratio of 1:40 with epoxide is incubated at room temperature with rocking for 12-16 hrs. The acetonitrile is removed under reduced pressure and the residue is dissolved in ethanol before purification via HPLC. Purification of 17,18-EEQ derivatives is performed using a reversed phase high-performance liquid chromatography (RP-HPLC), Sun Fire Prep C18 5 μm 19×50 mm (Waters, PN 186002566) and a mobile system composed of solvent A ($H_2O$/acetonitrile/acetic acid 95:5: 0.1) and solvent B ($H_2O$/acetonitrile/acetic acid 5:95:0.1) and a linear gradient from 50% A to 0% A in 50 minutes.

The following compounds were made using analogous procedures:

(5Z,8Z,11Z,14Z)-16-(3-ethyloxiran-2-yl)-N-(3-hydroxypropyl)hexadeca-5,8,11,14-tetraenamide (17,18-EEQ-NA). Synthesis was performed as mentioned in the previous section using 17,18-EEQ and 3-amino-1-propanol. HR-ESI-MS (m/z) found: 376.3, $[M+H]^+$ calculated $C_{23}H_{37}NO_3$: 375.54.

(5Z,8Z,11Z,14Z)-16-(3-ethyloxiran-2-yl)-N-(1-hydroxypropan-2-yl)hexadeca-5,8,11,14-tetraenamide (17,18-EEQ-IA). Synthesis was performed as mentioned in the previous section using 17,18-EEQ and R-(−)2-amino-1-propanol. HR-ESI-MS (m/z) found: 376.3, $[M+H]^+$ calculated $C_{23}H_{37}NO_3$: 375.54.

Example 2. Synthesis of Aziridine Derivatives

Scheme 2 shows a representative conversion of a 17,18-EEQ epoxide to the corresponding aziridine. The epoxide may be converted to azide with sodium azide and ammonium chloride and then reduced with triphenylphosphine to produce the corresponding aziridine. This process may also be applied to the synthesis of compounds having an aziridine at the 5, 6, 8, 9, 11, 12, or 14, 15 positions.

Scheme 2

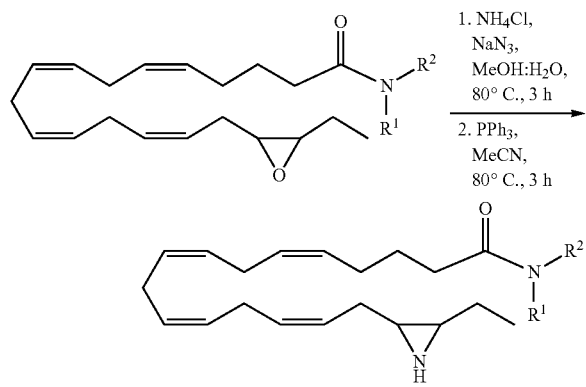

To a stirred solution of sodium azide (2 equivalents) and ammonium chloride (3 equiv) in water at room temperature a solution of epoxide (1 equiv) is added in MeOH and then the reaction is stirred at 80° C. for 3 h. After the solution is cooled to room temperature, the excess of MeOH is removed under reduced pressure and the residue is diluted with EtOAc, washed with water, dried over anhydrous sodium sulfate and concentrated under reduced pressure to give a brown oil. Filtration on a pad of silica gel (hexane/EtOAc 4:1) gives the nitrile that is taken forward for the next reaction. A solution of nitrile in anhydrous acetonitrile is heated to reflux under nitrogen atmosphere. Next, triphenylphosphine (20 equiv), is added immediately and the reaction is stirred under reflux for 3 h. After cooling to room temperature, the mixture is concentrated under reduced pressure and purified by column chromatography on silica gel (hexane/EtOAc 7:3).

Example 3. Synthesis of Thiirane Derivatives

A representative conversion of a 17,18-EEQ epoxide to corresponding thiirane in the presence of potassium thiocyanate and oxalic acid in a commercial microwave is shown Scheme 3. This process may also be applied to the synthesis of compounds having a thiirane at the 5, 6, 8, 9, 11, 12, or 14, 15 positions.

Scheme 3

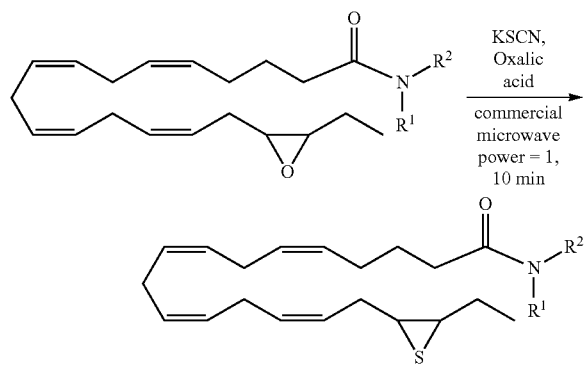

To a solution of amide derivative in methanol, KSCN and oxalic acid are added and heated in a commercial microwave at power 1 for 10 mins. The reaction mixture is cooled and concentrated in vacuo. The mixture is purified using normal phase HPLC using 90% hexane 10% isopropanol as the eluent.

Example 4. Anti-inflammatory Assay in BV-2 Microglial Cells

Figure 2:
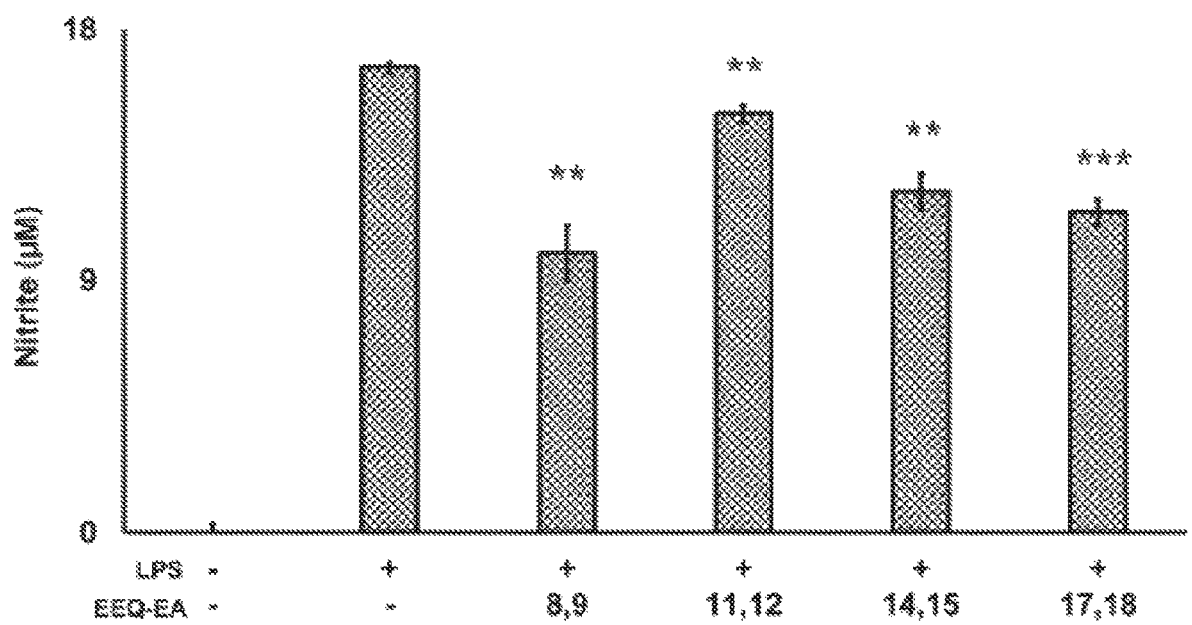
FIG. 2 shows EEQ-EA regioisomers role in neuroinflammation. BV-2 microglial cells were pre-incubated with EEQ-EA regioisomers (2.5 µM) for 4 hours followed by LPS (25 ng/mL) stimulation. Culture medium was collected after 24 hours and analyzed for proinflammatory NO (n=3). Significant P values are indicated as * (P≤0.001),  (P≤0.01), and * (P≤0.05).
Figure 3A:
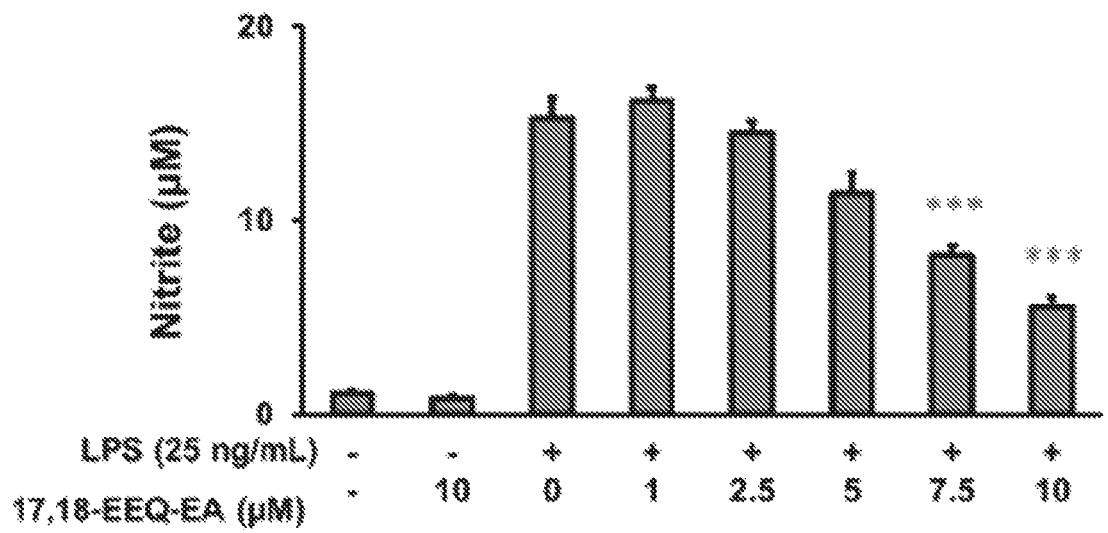
FIG. 3A, FIG. 3B, FIG. 3C and FIG. 3D show the dose-dependent NO and Il-6 studies for 17,18-EEQ-EA and 8,9-EEQ-EA. BV-2 microglial cells were pre-incubated with varying concentrations of 17,18-EEQ-EA or 8,9-EEQ-EA for 4 hours followed by LPS (25 ng/mL) stimulation. Culture medium was collected after 24 hours and analyzed for NO (A, C) and IL-6 (B, D) production. Significant P values are indicated as * (P≤0.001),  (P≤0.01), and * (P≤0.05). Values are expressed as mean±SEM and +/− indicates LPS added or LPS not added. * represents P<0.05,  represents P<0.01, * represents P<0.001, **** represents P<0.0001 relative to LPS.
Figure 3B:
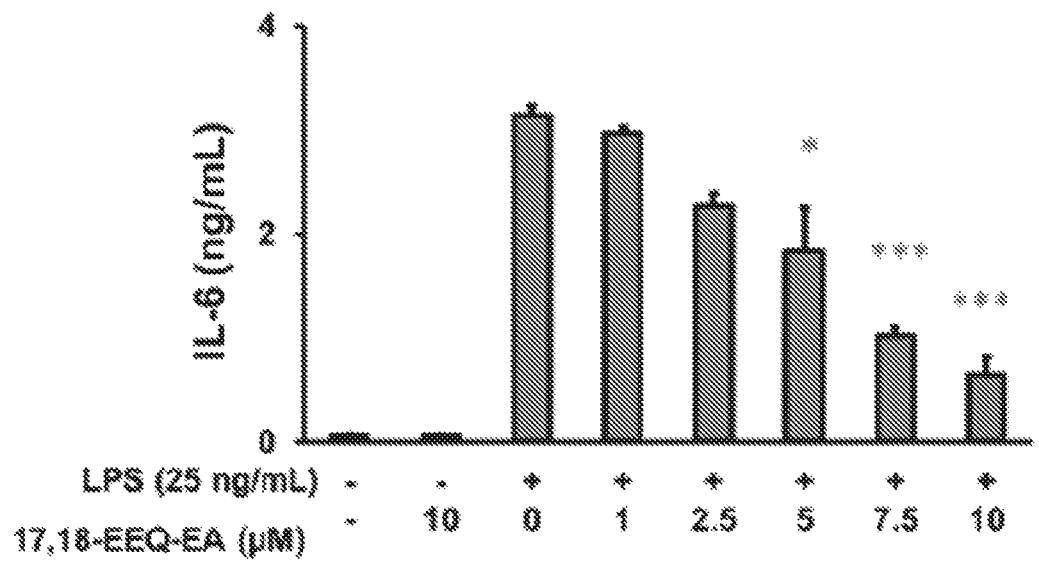
Figure 3C:
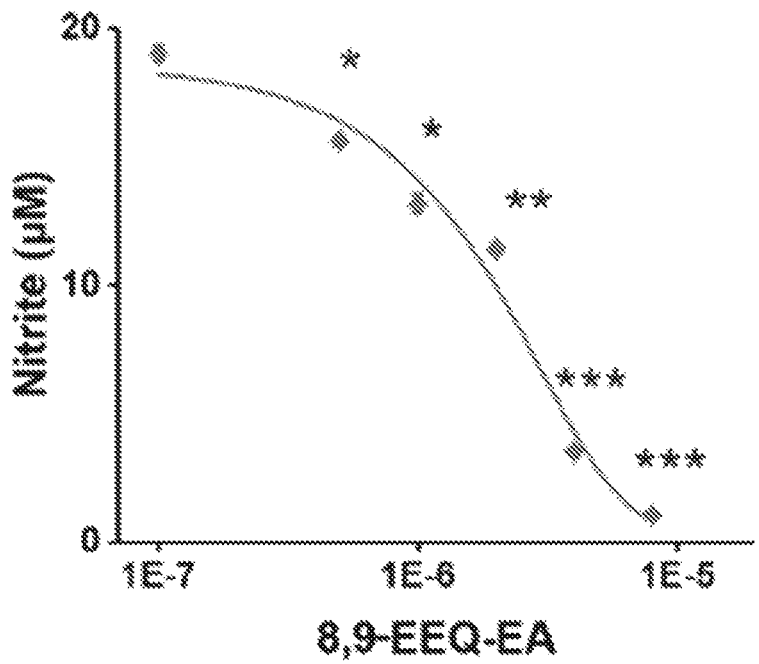
Figure 3D:
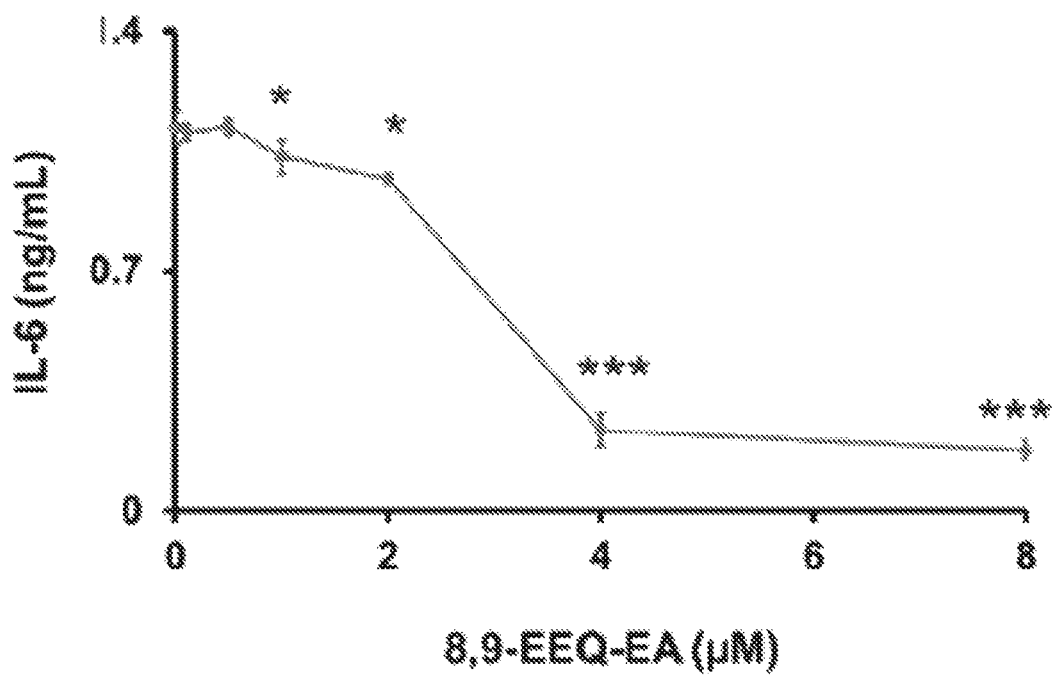

Experiments were performed with mouse BV-2 microglial cells. Cells were grown and maintained in Dulbecco's modified Eagle's medium supplemented with 10% fetal bovine serum, 1% streptomycin and penicillin at 37° C. in a 5% $CO_2$ humidified air atmosphere. BV-2 cells were seeded in 24-well plates (200K cells/mL) and grown to 80-90% confluency. For regioisomer screening and dose response studies, media was replaced with serum-free media and the cells were pre-incubated with regioisomers for 4 hours prior to stimulation with 25 ng/mL LPS (Sigma-Aldrich, USA). To determine nitrite and IL-6 production, media was collected at 24 hours and the production of nitric oxide (NO) was determined by using the Greiss method and IL-6 secretion was measured using ELISA (no. 583371; Cayman Chemical). All isomers of EPEA epoxides, EEQ-EA, showed reduction in NO formation (FIG. 2, FIG. 3A and FIG. 3B). For IL-6 studies, both 17,18-EEQ-EA (FIG. 3D) and 8,9-EEQ-EA (FIG. 3C) reduced IL-6 in a dose-dependent manner.

Figure 4A:
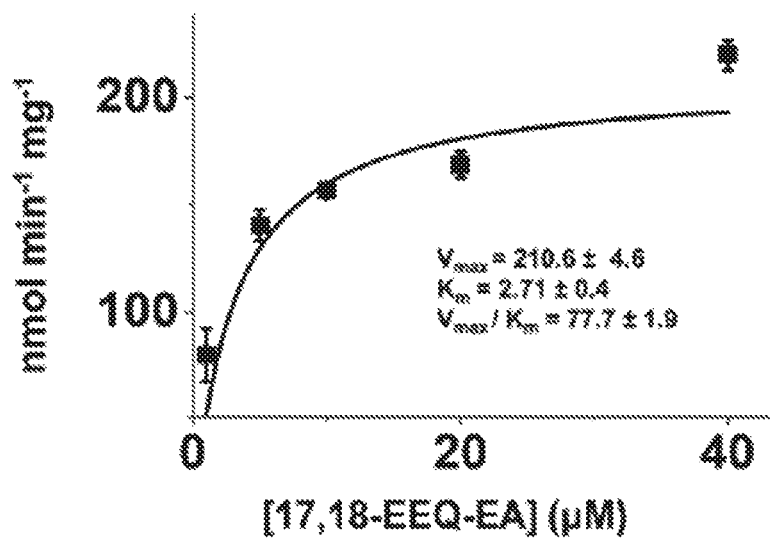
FIG. 4A, FIG. 4B, FIG. 4C and FIG. 4D show FAAH (FIG. 4B and FIG. 4D) and sEH (FIG. 4A and FIG. 4C) hydrolysis of 17,18-EEQ-EA and 8,9-EEQ-EA, respectively. To determine the rate of hydrolysis by sEH, increasing substrate (8,9-EEQ-EA) concentrations were incubated at 37° C. with sEH ($[E]_{final}$=6 nM). For $V_{max}$ and $K_m$ values, plots were fitted to the Michaelis-Menten equation using Origin Pro. For FAAH hydrolysis, membranes from rat forebrain tissue were isolated for time-based hydrolysis. Incubations were performed with 100 µg of forebrain protein and 50 µM of substrate for 5, 20 and 40 minutes at 37° C. Both reactions were measured for product conversion using LC-MS/MS.
Figure 4B:
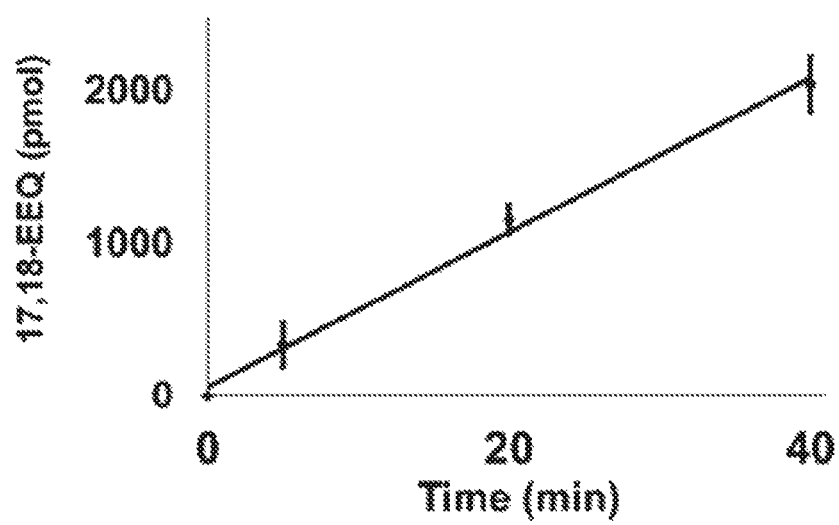
Figure 4C:
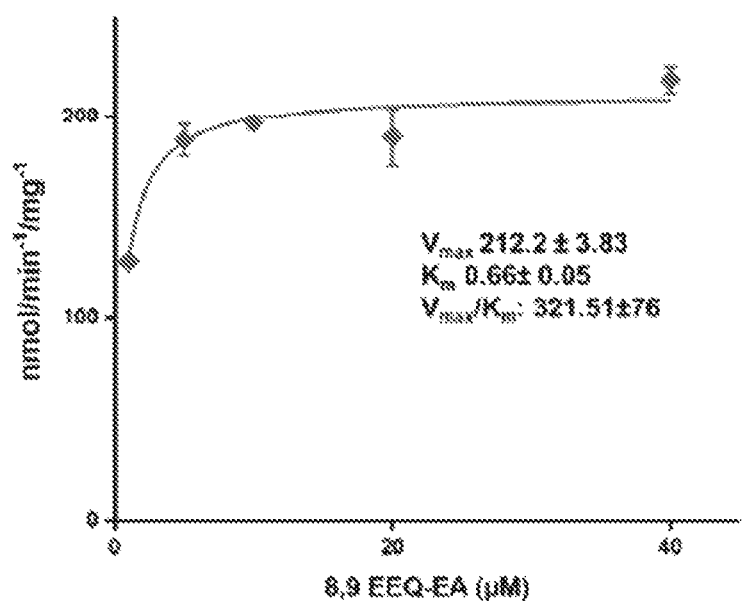

Example 5. Susceptibility to FAAH and sEH Hydrolysis of 8,9- and 17,18-EEQ-EA For soluble epoxide hydrolase (sEH) kinetics, increasing concentrations of substrates (8,9-EEQ-EA (FIG. 4C) and 17,18-EEQ-EA (FIG. 4A)) were incubated with recombinant sEH (final [6 nM]) in a 0.1 mL reaction containing $NaPO_4$ (0.1 M, pH 7.4), bovine serum albumin (0.1 mg/ml) at 37° C. The enzymatic reaction was stopped after 5 min with equal volume of methanol with AUDA (0.5 μM) and centrifuged at 10,000 g for 10 min. The supernatant was saved and quantitated using LC-MS/MS. Data was fit to kinetic curves and the Michaelis-Menten equation was used to calculate $V_{max}$ and $K_m$. Compared to the terminal 17,18-EEQ-EA, 8,9-EEQ-EA showed a faster rate of hydrolysis with turnover rate of $(V_{max}/K_m)$ 321.51±76 nmol min-1 mg-1 of sEH, 4 times that of 17,18 EEQ-EA (77.7±1.9 nmol min-1 mg-1 of sEH).

Figure 4D:
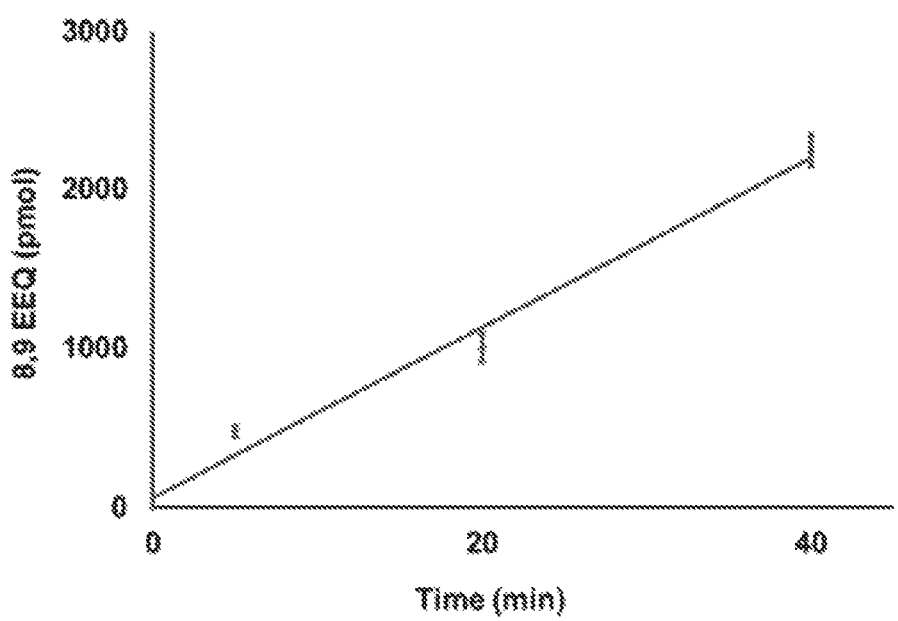

For fatty acid amide hydrolase (FAAH) kinetics (FIG. 4B and FIG. 4D), rat forebrain membranes were homogenized in buffer (50 mM Tris pH 7.4, 1 mM EDTA and 3 mM $MgCl_2$) and membrane pellet was collected as previously described. 8,9-EEQ-EA or 13,14-EDP-EA (50 μM) was incubated with 100 μg forebrain membrane containing 50 mM Tris (pH 7.4), 1 mM EDTA, 3 mM $MgCl_2$ in a 0.5 mL reaction. Linearity of the reactions was confirmed at 5, 20 and 40 minutes. Reactions were stopped with methanol containing 1 mM PMSF and centrifuged at 10,000 g for 10 min to collect supernatant via LC-MS/MS. Hydrolysis from 8,9-EEQ-EA to corresponding 8,9-EEQ was comparable to the rate of 17, 18-EEQ-EA to 17,18-EEQ.

Example 6. Presto-Tango β-arrestin Recruitment Assay

Figure 5A:
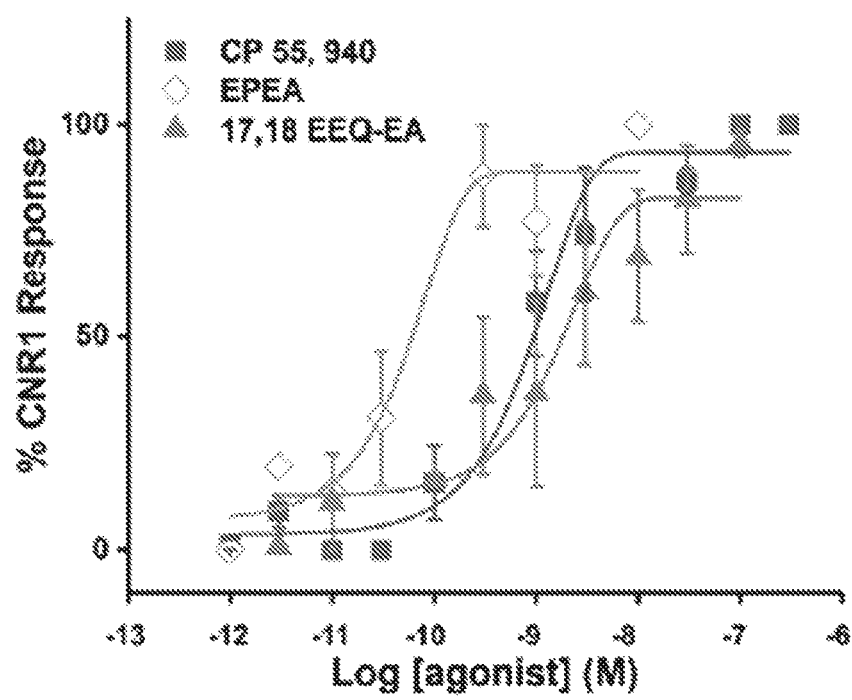
FIG. 5A and FIG. 5B show dose-response curves for cannabinoid receptor 1 (CNR1) and cannabinoid receptor 2 (CNR2), respectively. The dose response curves were generated by monitoring the relative luminescence of cannabinoid receptor 1 (CNR1) and cannabinoid receptor 2 (CNR2) of PRESTO-Tango gene-transfected HTLA cells for 17,18-EEQ-EA, EPEA, and CP 55940. Values shown are the mean±SEM of experiments performed multiple times (n=3-7) *P<0.05, P<0.01, and *P<0.001.
Figure 5B:
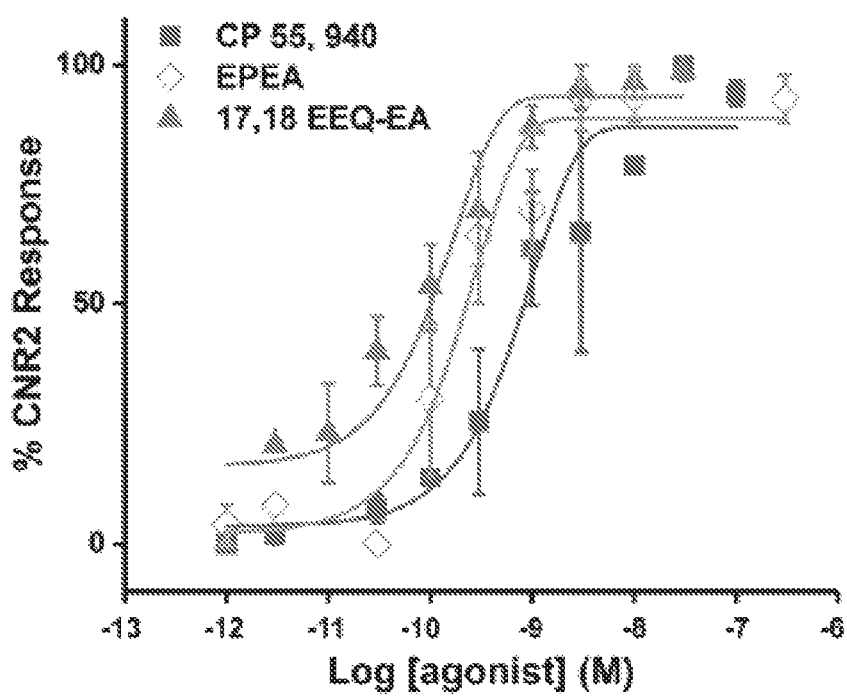

Binding of the parent compounds to putative receptors CNR1 and CNR2 (cannabinoid receptors 1 & 2) was measured by a Presto-Tango assay (FIG. 5A and FIG. 5B, respectively). These receptors are responsible for many downstream effects of marijuana derivatives as well as other endocannabinoids that have been previously reported in literature and this study explores if our compounds bind to these receptors. HTLA cells were received from the Roth Lab and CNR1 and CNR2 plasmids were purchased from Addgene. HTLA cells were maintained in DMEM with 10% FBS containing 2 μg/mL of puromycin and 100 μg/mL of hygromycin B at 37° C. in a 5% $CO_2$ humidified air atmosphere and grown to 80-90% confluency. Cells were then seeded at 20,000 cells per 100 μL into poly-L-lysine coated 96-well plate. After 18-24 hours, cells were transfected with CNR2 (0.1 μg/well) using Calfectin as the transfection reagent. Transfection media was replaced after 12-18 hours with serum-media and proceeded for ~36 hours. For epoxygenated metabolites, serum-media was replaced with 100 μL media containing 1% dialyzed FBS and 1 μM AUDA for 30 min, then compound was further diluted with media containing 1% dialyzed FBS and was added in a log dose manner (final well vol. 200 μL including the media with AUDA) and incubated for 8-14 hours. The following day, media was removed and 40 μL of diluted Bright-Glo solution (Promega, Madison. Wis.) was added to each well and incubated in the dark for 20 min at room temperature before luminescence recordings. Relative luminescence units (RLU) values were normalized to % receptor response, plotted as a function of compound concentration and analyzed using "DoseResp" in OriginPro. EPEA epoxide 17,18-EEQ-EA activate CNR2 ($EC_{50}$=1.4 nM) more significantly than CNR1 ($EC_{50}$=18.5 nM).

For reasons of completeness, various aspects of the invention are set out in the following numbered clauses:

Clause 1. A compound of formula (I), or a pharmaceutically acceptable salt thereof,

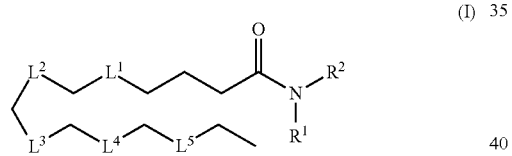

(I)

wherein,
one of $L^1$, $L^2$, $L^3$, $L^4$, and $L^5$ is

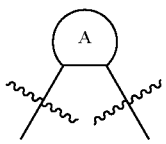

and the others of $L^1$, $L^2$, $L^3$, $L^4$, and $L^5$ are

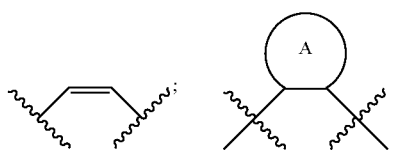

is 3- to 6-membered ring containing at least one heteroatom selected from the group consisting of oxygen, nitrogen, and sulfur;
$R^1$ is hydrogen, $C_{1-6}$alkyl, $C_{1-6}$haloalkyl, —$C_{1-6}$alkylene-$R^{x1}$, -$G^1$, or —$C_{1-6}$alkylene-$G^1$;

$G^1$ is $C_{3-8}$cycloalkyl, $C_{3-8}$cycloalkenyl, aryl, heteroaryl, or heterocycle, wherein $G^1$ is optionally substituted with 1, 2, 3, or 4 $R^{x1}$;
$R^2$ is $C_{1-6}$alkyl, $C_{1-6}$haloalkyl, —$C_{1-6}$alkylene-$R^{x2}$, -$G^2$, or —$C_{1-6}$alkylene-$G^2$;
$G^2$ is $C_{3-8}$cycloalkyl, $C_{3-8}$cycloalkenyl, aryl, heteroaryl, or heterocycle, wherein $G^2$ is optionally substituted with 1, 2, 3, or 4 $R^{x2}$;
$R^{x1}$ and $R^{x2}$ at each occurrence are independently cyano, —OH, —$OC_{1-4}$alkyl, —$OC(O)C_{1-4}$alkyl, —$NH_2$, —$NHC_{1-4}$alkyl, —$N(C_{1-4}$alkyl$)_2$, —$NHC(O)C_{1-4}$alkyl, or —$N(C_{1-4}$alkyl$)C(O)C_{1-4}$alkyl;
provided that $R^2$ is not —$CH_2CH_2OH$ when

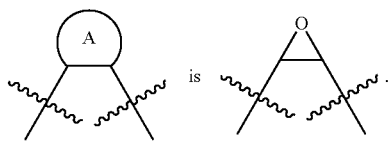

Clause 2. The compound of clause 1, or a pharmaceutically acceptable salt thereof, wherein

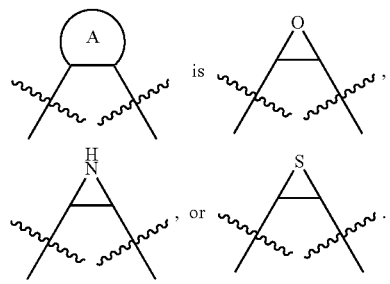

Clause 3. The compound of any one of clauses 1-2, or a pharmaceutically acceptable salt thereof, wherein $R^1$ is hydrogen.

Clause 4. The compound of any one of clauses 1-3, or a pharmaceutically acceptable salt thereof, wherein $R^2$ is $C_{1-6}$alkyl, —$C_{1-6}$alkylene-$R^{x2}$, -$G^2$, or —$C_{1-6}$alkylene-$G^2$.

Clause 5. The compound of any one of clauses 1-4, or a pharmaceutically acceptable salt thereof, wherein $R^2$ is —$C_{1-6}$alkylene-$R^{x2}$.

Clause 6. The compound of any one of clauses 1-4, or a pharmaceutically acceptable salt thereof, wherein
$R^2$ is -$G^2$ or —$C_{1-6}$alkylene-$G^2$, and
$G^2$ is $C_{3-8}$cycloalkyl optionally substituted with 1, 2, 3, or 4 $R^{x2}$.

Clause 7. The compound of clause 6, or a pharmaceutically acceptable salt thereof, wherein G2 is

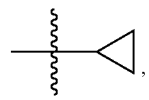 [SMILES: *C1CC1]

which is optionally substituted with 1, 2, or 3 $R^{x2}$.

Clause 8. The compound of any one of clauses 1-7, or a pharmaceutically acceptable salt thereof, wherein $R^{x2}$ at each occurrence is independently —OH or —$NH_2$.

Clause 9. The compound of any one of clauses 1-7, or a pharmaceutically acceptable salt thereof, wherein $R^2$ is

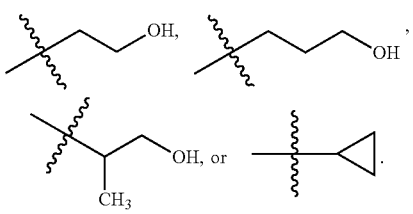

Clause 10. The compound of clause 1, selected from the group consisting of

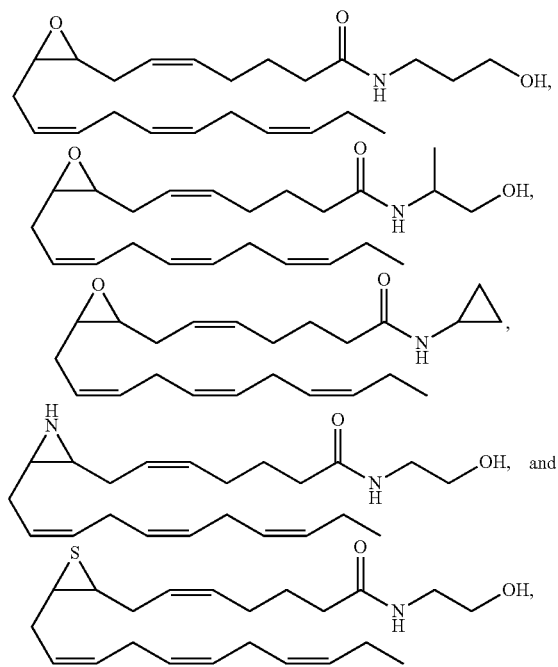

or a pharmaceutically acceptable salt thereof.

Clause 11. A pharmaceutical composition comprising a therapeutically effective amount of a compound of any one of clauses 1-10, or a pharmaceutically acceptable salt thereof, and a pharmaceutically acceptable carrier.

Clause 12. The compound of any one of clauses 1-10, or a pharmaceutically acceptable salt thereof, for use in treating cancer.

Clause 13. The compound of any one of clauses 1-10, or a pharmaceutically acceptable salt thereof, for use in reducing inflammation in a subject.

Clause 14. The compound of any one of clauses 1-10, or a pharmaceutically acceptable salt thereof, for use in reducing platelet aggregation in a subject.

Clause 15. The compound of any one of clauses 1-10, or a pharmaceutically acceptable salt thereof, for use in reducing angiogenesis in a subject.

Clause 16. The compound of any one of clauses 1-10, or a pharmaceutically acceptable salt thereof, for use in inducing vasoconstriction or vasodilation in a subject.

Clause 17. Use of a compound of any one of clauses 1-10, or a pharmaceutically acceptable salt thereof, for manufacturing a medicament for treating cancer.

Clause 18. Use of a compound of any one of clauses 1-10, or a pharmaceutically acceptable salt thereof, for manufacturing a medicament for reducing inflammation in a subject.

Clause 19. Use of a compound of any one of clauses 1-10, or a pharmaceutically acceptable salt thereof, for manufacturing a medicament for reducing platelet aggregation in a subject.

Clause 20. Use of a compound of any one of clauses 1-10, or a pharmaceutically acceptable salt thereof, for manufacturing a medicament for reducing angiogenesis in a subject.

Clause 21. Use of a compound of any one of clauses 1-10, or a pharmaceutically acceptable salt thereof, for manufacturing a medicament for inducing vasoconstriction or vasodilation in a subject.

Clause 22. A method of treating cancer comprising administering to a subject in need thereof a therapeutically effective amount of a compound of any one of clauses 1-10, or a pharmaceutically acceptable salt thereof, or a pharmaceutical composition of clause 11.

Clause 23. A method of reducing inflammation comprising administering to a subject in need thereof a therapeutically effective amount of a compound of any one of clauses 1-10, or a pharmaceutically acceptable salt thereof, or a pharmaceutical composition of clause 11.

Clause 24. A method for reducing platelet aggregation comprising administering to a subject in need thereof a therapeutically effective amount of a compound of any one of clauses 1-10, or a pharmaceutically acceptable salt thereof, or a pharmaceutical composition of clause 11.

Clause 25. A method of reducing angiogenesis comprising administering to a subject in need thereof a therapeutically effective amount of a compound of any one of clauses 1-10, or a pharmaceutically acceptable salt thereof, or a pharmaceutical composition of clause 11.

Clause 26. A method of inducing vasoconstriction vasodilation comprising administering to a subject in need thereof a therapeutically effective amount of a compound of any one of clauses 1-10, or a pharmaceutically acceptable salt thereof, or a pharmaceutical composition of clause 11.

The invention claimed is:
1. A compound of formula

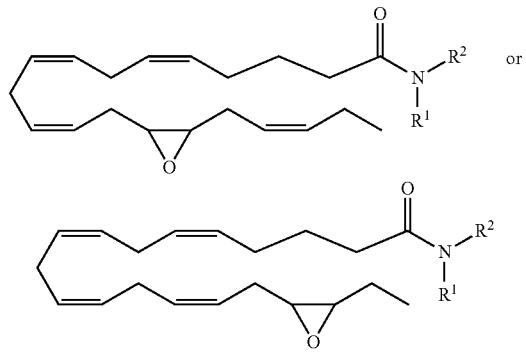

or a pharmaceutically acceptable salt thereof,
wherein,
$R^1$ is hydrogen, $C_{1-6}$alkyl, $C_{1-6}$haloalkyl, —$C_{1-6}$alkylene-$R^{x1}$, -$G^1$, or —$C_{1-6}$alkylene-$G^1$;
$G^1$ is $C_{3-8}$cycloalkyl, $C_{3-8}$cycloalkenyl, aryl, heteroaryl, or heterocycle, wherein $G^1$ is optionally substituted with 1, 2, 3, or 4 $R^{x1}$;
$R^2$ is -$G^2$ or —$C_{1-6}$alkylene-$G^2$;
$G^2$ is $C_{3-8}$cycloalkyl optionally substituted with 1, 2, 3, or 4 $R^{x2}$; and
$R^{x1}$ and $R^{x2}$ at each occurrence are independently cyano, —OH, —O$C_{1-4}$alkyl, —OC(O)$C_{1-4}$alkyl, —NH$_2$, —NHC$_{1-4}$alkyl, —N(C$_{1-4}$alkyl)$_2$, —NHC(O)C$_{1-4}$alkyl, or —N(C$_{1-4}$alkyl)C(O)C$_{1-4}$alkyl.

2. The compound of claim 1, or a pharmaceutically acceptable salt thereof, wherein R$^1$ is hydrogen.

3. The compound of claim 2, or a pharmaceutically acceptable salt thereof, wherein G$^2$ is

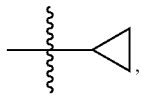

which is optionally substituted with 1, 2, or 3 R$^{x2}$, and R$^{x2}$ at each occurrence is independently —OH or —NH$_2$.

4. A compound of formula (I), or a pharmaceutically acceptable salt thereof,

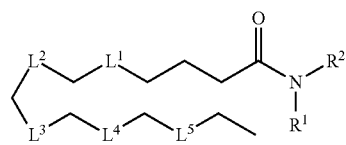

(I)

wherein, one of L$^1$, L$^2$, L$^3$, L$^4$, and L$^5$ is

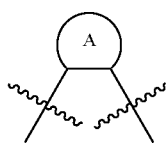

and the others of L$^1$, L$^2$, L$^3$, L$^4$, and L$^5$ are

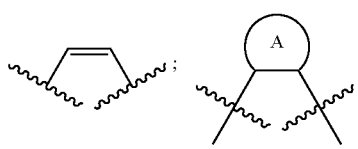

is 3- to 6-membered ring containing at least one heteroatom selected from the group consisting of oxygen, nitrogen, and sulfur;

R$^1$ is hydrogen, C$_{1-6}$alkyl, C$_{1-6}$haloalkyl, —C$_{1-6}$alkylene-R$^{x1}$, -G$^1$, or —C$_{1-6}$alkylene-G$^1$;

G$^1$ is C$_{3-8}$cycloalkyl, C$_{3-8}$cycloalkenyl, aryl, heteroaryl, or heterocycle, wherein G$^1$ is optionally substituted with 1, 2, 3, or 4 R$^{x1}$;

R$^2$ is C$_{1-6}$alkyl, C$_{1-6}$haloalkyl, —C$_{1-6}$alkylene-R$^{x2}$, -G$^2$, or —C$_{1-6}$alkylene-G$^2$;

G$^2$ is C$_{3-8}$cycloalkyl, C$_{3-8}$cycloalkenyl, aryl, heteroaryl, or heterocycle, wherein G$^2$ is optionally substituted with 1, 2, 3, or 4 R$^{x2}$;

R$^{x1}$ and R$^{x2}$ at each occurrence are independently cyano, —OH, —OC$_{1-4}$alkyl, —OC(O)C$_{1-4}$alkyl, —NH$_2$, —NHC$_{1-4}$alkyl, —N(C$_{1-4}$alkyl)$_2$, —NHC(O)C$_{1-4}$alkyl, or —N(C$_{1-4}$alkyl)C(O)C$_{1-4}$alkyl;

provided that:

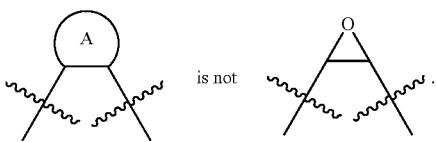

5. The compound of claim 4, or a pharmaceutically acceptable salt thereof, wherein

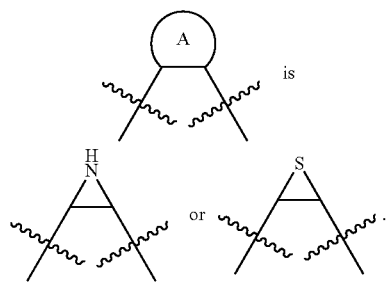

6. The compound of claim 5, or a pharmaceutically acceptable salt thereof, wherein R$^1$ is hydrogen.

7. The compound of claim 6, or a pharmaceutically acceptable salt thereof, wherein:

R$^2$ is —C$_{1-6}$alkylene-R$^{x2}$, -G$^2$, or —C$_{1-6}$alkylene-G$^2$;

G$^2$ is C$_{3-8}$cycloalkyl optionally substituted with 1, 2, 3, or 4 R$^{x2}$; and R$^{x2}$, at each occurrence, is independently —OH or —NH$_2$.

8. The compound of claim 7, or a pharmaceutically acceptable salt thereof, wherein R$^2$ is

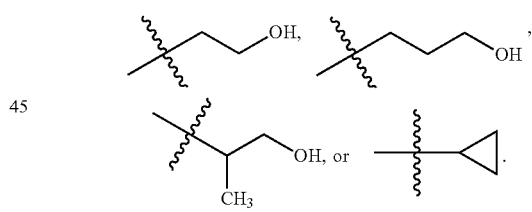

9. The compound of claim 7, or a pharmaceutically acceptable salt thereof, wherein the compound of formula (I) has formula (I-aa)

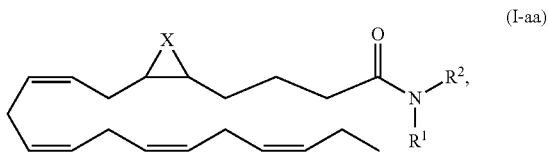

(I-aa)

wherein X is NH or S.

10. The compound of claim 7, or a pharmaceutically acceptable salt thereof, wherein the compound of formula (I) has formula (I-ba)

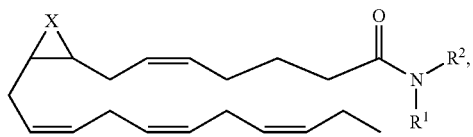
(I-ba)

wherein X is NH or S.

11. The compound of claim 7, or a pharmaceutically acceptable salt thereof, wherein the compound of formula (I) has formula (I-ca)

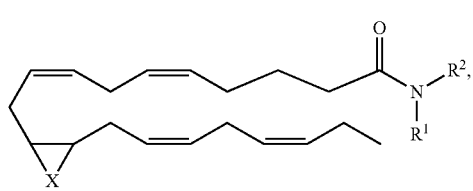
(I-ca)

wherein X is NH or S.

12. The compound of claim 7, or a pharmaceutically acceptable salt thereof, wherein the compound of formula (I) has formula (I-da)

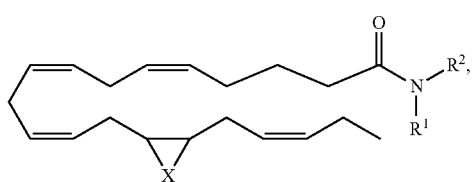
(I-da)

wherein X is NH or S.

13. The compound of claim 7, or a pharmaceutically acceptable salt thereof, wherein the compound of formula (I) has formula (I-ea)

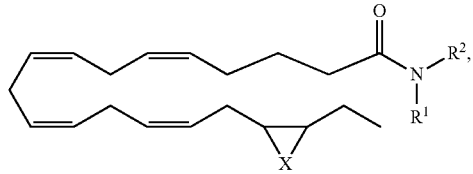
(I-ea)

wherein X is NH or S.

14. The compound of claim 7, selected from the group consisting of

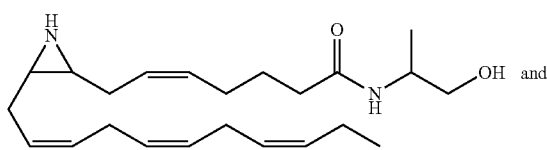

and

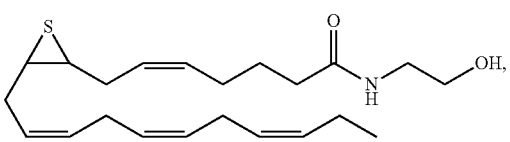

or a pharmaceutically acceptable salt thereof.

15. A pharmaceutical composition comprising a compound of claim 7, or a pharmaceutically acceptable salt thereof, and a pharmaceutically acceptable carrier.

16. A method of treating cancer comprising administering to a subject in need thereof a therapeutically effective amount of a compound of claim 7, or a pharmaceutically acceptable salt thereof.

17. A method of reducing inflammation comprising administering to a subject in need thereof a therapeutically effective amount of a compound of claim 7, or a pharmaceutically acceptable salt thereof.

18. A method for reducing platelet aggregation comprising administering to a subject in need thereof a therapeutically effective amount of a compound of claim 7, or a pharmaceutically acceptable salt thereof.

19. A method of reducing angiogenesis comprising administering to a subject in need thereof a therapeutically effective amount of a compound of claim 7, or a pharmaceutically acceptable salt thereof.

20. A method of inducing vasoconstriction or vasodilation comprising administering to a subject in need thereof a therapeutically effective amount of a compound of claim 7, or a pharmaceutically acceptable salt thereof.

* * * * *